US007835786B2

(12) United States Patent
Palmer et al.

(10) Patent No.: US 7,835,786 B2
(45) Date of Patent: Nov. 16, 2010

(54) METHODS, SYSTEMS, AND COMPUTER PROGRAM PRODUCTS FOR OPTIMIZATION OF PROBES FOR SPECTROSCOPIC MEASUREMENT IN TURBID MEDIA

(75) Inventors: Gregory M. Palmer, Durham, NC (US); Nirmala Ramanujam, Chapel Hill, NC (US)

(73) Assignees: Wisconsin Alumni Research Foundation, Madison, WI (US); Duke University, Durham, NC (US)

( * ) Notice: Subject to any disclaimer, the term of this patent is extended or adjusted under 35 U.S.C. 154(b) by 644 days.

(21) Appl. No.: 11/493,020

(22) Filed: Jul. 25, 2006

(65) Prior Publication Data

US 2007/0019199 A1 Jan. 25, 2007

Related U.S. Application Data

(60) Provisional application No. 60/702,228, filed on Jul. 25, 2005.

(51) Int. Cl.
*A61B 6/00* (2006.01)
*G01J 3/30* (2006.01)
*G02B 6/06* (2006.01)

(52) U.S. Cl. .................. 600/477; 600/476; 356/317; 385/116

(58) Field of Classification Search .................. None
See application file for complete search history.

(56) References Cited

U.S. PATENT DOCUMENTS

| 4,580,895 | A | 4/1986 | Patel |
| 5,203,328 | A | 4/1993 | Samuels et al. |
| 5,439,578 | A | 8/1995 | Dovichi et al. |

(Continued)

FOREIGN PATENT DOCUMENTS

WO    WO 02/40971 A1    5/2002

(Continued)

OTHER PUBLICATIONS

Notification of Transmittal of the International Search Report and the Written Opinion of the International Searching Authority, or the Declaration for International Application No. PCT/US06/28770 (Mar. 12, 2008).

(Continued)

*Primary Examiner*—Long V Le
*Assistant Examiner*—Angela M Hoffa
(74) *Attorney, Agent, or Firm*—Jenkins, Wilson, Taylor & Hunt, P.A.

(57) ABSTRACT

Methods, systems, and computer program products for optimizing a probe geometry for spectroscopic measurement in a turbid medium are provided. A probe geometry comprising one emitting entity and at least on collecting entity is selected. A simulation is performed to generate optical parameter values measured by the probe geometry. The measured optical parameter values are input to an inversion algorithm to produce corresponding optical properties as output. The produced optical properties are compared with known optical properties known and a degree of matching between the produced optical properties and the known optical properties is determined. The simulation and inversion steps are repeated for a plurality of additional probe geometries, each differing in at least one property. An optimization algorithm is applied at each iteration to select an optimal probe geometry.

22 Claims, 9 Drawing Sheets

U.S. PATENT DOCUMENTS

| | | | |
|---|---|---|---|
| 5,452,723 | A | 9/1995 | Wu et al. |
| 5,529,391 | A | 6/1996 | Kindman et al. |
| 5,582,168 | A | 12/1996 | Samuels et al. |
| 5,813,403 | A * | 9/1998 | Soller et al. ............... 600/310 |
| 5,924,981 | A | 7/1999 | Rothfritz et al. |
| 5,953,477 | A * | 9/1999 | Wach et al. ................ 385/115 |
| 5,976,892 | A | 11/1999 | Bisconte |
| 6,055,451 | A | 4/2000 | Bambot et al. |
| 6,219,566 | B1 | 4/2001 | Weersink et al. |
| 6,411,373 | B1 | 6/2002 | Garside et al. |
| 6,564,088 | B1 * | 5/2003 | Soller et al. ................ 600/478 |
| 6,571,118 | B1 | 5/2003 | Utzinger et al. |
| 6,577,391 | B1 | 6/2003 | Faupel et al. |
| 6,590,651 | B1 | 7/2003 | Bambot et al. |
| 6,678,541 | B1 | 1/2004 | Durkin et al. |
| 6,813,515 | B2 | 11/2004 | Hashimshony |
| 6,850,656 | B1 | 2/2005 | Bevilacqua et al. |
| 6,870,620 | B2 | 3/2005 | Faupel et al. |
| 6,912,412 | B2 * | 6/2005 | Georgakoudi et al. ....... 600/310 |
| 6,965,345 | B2 | 11/2005 | Bae et al. |
| 6,975,899 | B2 | 12/2005 | Faupel et al. |
| 7,006,220 | B2 | 2/2006 | Bambot et al. |
| 7,030,988 | B2 | 4/2006 | Kubo et al. |
| 7,062,333 | B2 | 6/2006 | Mizutani |
| 7,064,837 | B2 | 6/2006 | Mori et al. |
| 7,082,325 | B2 | 7/2006 | Hashimshony et al. |
| 7,113,624 | B2 | 9/2006 | Curry |
| 7,129,454 | B2 | 10/2006 | O'Connell et al. |
| 7,145,645 | B2 | 12/2006 | Blumenfeld et al. |
| 7,184,824 | B2 | 2/2007 | Hashimshony |
| 7,236,815 | B2 | 6/2007 | Richards-Kortum et al. |
| 7,411,680 | B2 | 8/2008 | Chang et al. |
| 7,751,039 | B2 | 7/2010 | Ramanujam et al. |
| 2002/0055671 | A1 | 5/2002 | Wu et al. |
| 2002/0084417 | A1 | 7/2002 | Khalil et al. |
| 2002/0114734 | A1 | 8/2002 | Pantoliano et al. |
| 2002/0193671 | A1 | 12/2002 | Ciurczak et al. |
| 2006/0247532 | A1 | 11/2006 | Ramanujam et al. |
| 2007/0232932 | A1 | 10/2007 | Palmer et al. |
| 2008/0056957 | A1 | 3/2008 | Hayman |
| 2008/0270091 | A1 | 10/2008 | Ramanujam et al. |
| 2009/0015826 | A1 | 1/2009 | Ramanujam et al. |

FOREIGN PATENT DOCUMENTS

| | | |
|---|---|---|
| WO | WO 2006/076810 A1 | 7/2006 |
| WO | WO 2007/014188 A2 | 2/2007 |
| WO | WO 2007/109126 A2 | 9/2007 |
| WO | WO 2008/103486 A1 | 8/2008 |
| WO | WO 2009/043045 A1 | 4/2009 |
| WO | WO 2009/043050 A2 | 4/2009 |
| WO | WO 2009/132360 A2 | 10/2009 |

OTHER PUBLICATIONS

Amelink et al., "Measurement of the Local Optical Properties of Turbid Media by Differential Path-Length Spectroscopy," Applied Optics, vol. 34, No. 15, pp. 3048-3054 (May 20, 2004).

Breslin et al., "Autofluorescence and Diffuse Reflectance Properties of Malignant and Benign Breast Tissues," Annals of Surgical Oncology, vol. 11, No. 1, pp. 65-70 (2003).

Mourant et al., "Measuring Absorption Coefficients in Small Volumes of Highly Scattering Media: Source-Detector Separations for Which Path Lengths do not Depend on Scattering Properties".

Interview Summary for U.S. Appl. No. 11/729,967 (Sep. 24, 2009).

Interview Summary for U.S. Appl. No. 11/725,141 (Nov. 17, 2009).

Notice of Allowance and Fee(s) Due for U.S. Appl. No. 11/729,967 (Oct. 22, 2009).

Liu et al., "Sequential Estimation of Optical Properties of a Two-layered Epithelial Tissue Model From Depth-Resolved Ultraviolet-visible Diffuse Relectance Spectra," Applied Optics, vol. 45, No. 19, pp. 4776-4790 (July 1, 2006).

Simonson et al., "Modulation of an Optical Needle's Reflectivity Alters the Average Photon Path Through Scattering Media," Journal of Biomedical Optics, vol. 11, No. 1, pp. 14-23 (Jan./Feb. 2006).

Pfefer et al., "Oblique-Incidence Illumination and Collection for Depth-Selective Fluorescence Spectroscopy," Journal of Biomedical Optics, vol. 10, No. 4, (Jul./Aug. 2005).

Zhu et al., "Use of A Multiseparation Fiber Optic Probe for the Optical Diagnosis of Breast Cancer," Journal of Biomedical Optics, vol. 10, No. 2, pp. 024032-1-024032-13 (Mar./Apr. 2005), In 180/212/2 Spec.

Wall, "GAlib: Matthew Wall's Genetic Algorithm Library," vol. 2005 (2005).

Manos et al., "Optical Fiber Design Using Evolutionary Strategies," Engineering Computations, vol. 21, No. 6, pp. 564-576 (2064).

Pfefer et al. "Influence of Illumination-Collection Geometry on Fluorescence Spectroscopy in Multilayer Tissue," Medical and Biological Engineering and Computing, vol. 42, No. 5, pp. 669-673 (Sep. 2004).

Liu et al., "Experimental Proof of the Feasibility of Using an Angled Fiber-optic Probe for Depth-sensitive Flurorescence Spectroscopy of Turbid Media," Optics Letters, vol. 29, No. 17, pp. 2034-2036 (Sep. 1, 2004).

Finlay et al., "Hemoglobin Oxygen Saturations in Phantoms and In Vivo From Measurements of Steady State Diffuse Reflectance at a Single, Short Source-detector Separation," Med Phys. vol. 31, No. 7, pp. 1949-1959 (Jul. 2004).

Palmer et al., "Comparison of Multiexcitation Fluorescence and Diffuse Reflectance Spectroscopy for the Diagnosis of Breast Cancer," Biomedical Engineering, vol. 50, Issue 11, pp. 1233-1242 (Nov. 2003).

Thueler et al;., "In Vivo Endoscopic Tissue Diagnostics Based on Spectroscopic Absorption, Scattering, and Phase Function Properties," Journal of Biomedical Optics, vol. 8, No. 3, pp. 495-503 (Jul. 2003).

Pfefer et al., "Reflectance-based Detemination of Optical Properties in Highly Attenuating Tissue," Journal of Biomedical Optics, vol. 8, Issue 2 (Apr. 2003).

Zhu et al., "Effect of Fiber Optic Probe Geometry on Depth-resolved Fluorescence Measurements From Epithelial Tissues: A Monte Carlo Simulation," Journal of Biomedical Optics, vol. 8, No. 2, p. 237-247 (Apr. 2003).

Eiben and Smith, "Introduction to Evolutionary Computing," Springer-Verlag, Natural Computing Series, New York, New York, p. 2-16, (2003).

Prahl, "Mie Scattering Program," vol. 2003 (Copyright 2007) (Downloaded from the Internet on Jan. 19, 2010).

Xiaoyan et al., "Determination of Complex Refractive Index of Polystyrene Microspheres From 370 to 1610 nm," Physicis in Medicine and Biology, vol. 48, p. 4165-4172 (2003).

Georgakoudi et al., "NAD(P)H and Collagen as inVivo Quantitative Fluorescent Biomarkers of Epithelial Precancerous Changes," Cancer Research, vol. 62, p. 682-687 (Feb. 1, 2002).

Zonios et al., "Diffuse Reflectance Spectroscopy of Human Adenomatous Colon Polyps In Vivo," Applied Optics, vol. 38, Issue 31, p. 6628-6637 (Nov. 1, 1999).

Pogue et al., "Fiber-Optic Bundle Design for Quantitative Fluorescence Measurement From Tissue," Applied Optics, vol. 37, Issue 31, p. 7429-7436 (Nov. 1, 1998).

Li et al., "Deriving the Integral Representation of a Fractional Hankel Transform From a Fractional Fourier Transform," vol. 23, No. 15, p. 1158-1160 (Aug. 1, 1998).

Kienle et al., "Determination of the Optical Properties of Turbid Media From a Single Monte Carlo Simulation," Physics in Medicine and Biology, vol. 41, Issue 10, p. 2221-2227 (Oct. 1996).

Chen et al., "Approximations of Continuous Functionals by Neural Networks With Application to Dynamic Systems," IEEE on Neural Networks, vol. 4, No. 6, p. 910-918 (Nov. 1993).

Cheong et al., "A Review of the Optical Properties of Biological Tissues," Quantum Electronics, vol. 26, No. 12 (Dec. 1990).

Bolin et al., "Refractive Index of Some Mammalian Tissues Using A Fiber Optic Cladding Method," Applied Optics, vol. 28, No. 12, pp. 2297-2303 (Jun. 15, 1989).

Official Action for U.S. Appl. No. 11/725,141 (Jun. 12, 2009).

Official Action for U.S. Appl. No. 11/729,967 (May 28, 2009).

PCT International Application Serial No. PCT/US09/41857 for "Systems and Methods for Performing Optical Spectroscopy Using a Self-Calibrating Fiber Optic Probe" (Apr. 27, 2009).

PCT International Application Serial No. PCT/US09/41732 for "A Diffuse Reflectance Spectroscopy Device for Quantifying Tissue Absorption and Scattering" (Apr. 24, 2009).

Restriction and/or Election Requirement for U.S. Appl. No. 11/729,967 (Apr. 17, 2009).

Notification of Transmittal of the International Search Report and the Written Opinion of the International Searching Authority, or the Declaration for International Application No. PCT/US2008/078194 (Apr. 17, 2009).

Notification of Transmittal of the International Search Report and the Written Opinion of the International Searching Authority, or the Declaration for International Application No. PCT/US2008/078186 (Feb. 17, 2009).

Communication of European Publication Number and Information on the Application of Article 67(3) EPC for European Patent No. 2001352 (Nov. 19, 2008).

Notification of Transmittal of the International Search Report and the Written Opinion of the International Searching Authority, or the Declaration for International Application No. PCT/US07/07586 (Oct. 7, 2008).

Notification of Transmittal of the International Search Report and the Written Opinion of the International Searching Authority, or the Declaration for International Application No. PCT/US08/02431 (Jun. 19, 2008).

Communication of European Publication Number and Information on the Application of Article 67(3) EPC for European Application No. 06800300.3 (Mar. 12, 2008).

Notification of Transmittal of the International Search Report and Written Opinion of the International Searching Authority, or the Declaration corresponding to PCT application No. PCT/US07/06624 (Feb. 7, 2008).

Liu et al., "Scaling Method for Fast Monte Carlo Simulation of Diffuse Reflectance Spectra from Multilayered Turbid Media," J. Opt. Soc. Am. A, vol. 24, No. 4, pp. 1011-1025 (Apr. 2007).

Palmer et al., "Monte Carlo-Based Inverse odel for Calculating Tissue Optical Properties. Part I: Theory and Valdiation on Synthetic Phantoms," Applied Optics, vol. 45, No. 5, pp. 1062-1071 (Feb. 10, 2006).

Palmer et al., "Monte Carlo-Based Inverse Model for Calculating Tissue Optical Properties. Part II: Application to Breast Cancer Diagnosis," Applied Optics, vol. 45, No. 5, pp. 1072-1078 (Feb. 10, 2006).

Zhu et al., "Diagnosis of Breast Cancer Using Diffuse Reflectance Spectroscopy: Comparison of a Monte Carlo Versus Partial Least Squares Analysis Based Feature Extraction Technique." Lasers in Surgery and Medicine, vol. 38, pp. 714-724 (2006).

Palmer, "Experimental, Computational, and Analytical Techniques for Diagnosing Breast Cancer Using Optical Spectroscopy," Dissertation, University of Wisconsin-Madison, pp. 1-188 (2005).

Chang et al., "Analytical Model to Describe Fluorescence Spectra of Normal and Preneoplastic Epithelial Tissue: Comparison with Monte Carlo Simulations and Clinical Measurements," Journal of Biomedical Optics, vol. 9, No. 3, pp. 511-522 (May/Jun. 2004).

Biswal et al., "Recovery of Turbidity Free Fluorescence from Measured Fluorescence: An Experimental Approach," Optics Express, vol. 11, No. 24, pp. 3320-3331 (Dec. 1, 2003).

Diamond et al., "Quantification of Fluorophore Concentration in Tissue-Simulating Media by Fluorescence Measurements with a Single Optical Fiber," Applied Optics, vol. 42, No. 13, pp. 2436-244 (May 1, 2003).

Swartling et al., "Accelerated Monte Carlo Models to Simulate Fluorescence Spectra from Layered Tissues," Journal of Optical Society of America, vol. 20, No. 4, pp. 714-727 (Apr. 2003).

Diamond et al., "Measurement of Fluorophore Concentrations and Fluorescence Quantum Yield in Tissue-Simulating Phantoms Using Three Diffusion Models of Steady-State Spatially Resolved Fluorescence," Physics in Medicine and Biology, vol. 48, pp. 4135-4149 (2003).

Ma et al., "Determination of Complex Refractive Index of Polystyrene Microspheres from 370 to 1610 nm," Physics in Medicine and Biology, vol. 48, pp. 4165-4172 (2003).

Weersink et al., "Noninvasive Measurement of Fluorophore Concentration in Turbid Media with a Simple Fluorescence/Reflectance Ratio Technique," Applied Optics, vol. 40, No. 34, pp. 6389-6395 (Dec. 1, 2001).

Muller et al., "Intrinsic Fluorescence Spectroscopy in Turbid Media: Disentangling Effects of Scattering and Absorption," Applied Optics, vol. 40, No. 25, pp. 4633-4646 (Sep. 1, 2001).

Ramanujam, "Fluorescence Spectroscopy in Vivo," Encyclopedia of Analytical Chemistry, pp. 20-56 (2000).

Yu et al., "Quasi-Discrete Henkel Transform," Optical Letters, vol. 23, No. 6, pp. 409-411 (Mar. 15, 1998).

Chance et al., "Biochemical Distinctions Between Normal and Cancerous Human Breast Tissues Obtained from Fluorescence Spectroscopy," Proceedings of Optical Tomography and Spectroscopy of Tissue: Theory, Instrumentation, Model, and Human Studies II, Biomedical Optics, vol. 2979, pp. 585-588 (Feb. 9-12, 1997).

Zhang et al., "Innate Cellular Fluorescence Reflects Alterations in Cellular Proliferation," Lasers in Surgery and Medicine, vol. 20, pp. 319-331 (1997).

Gardner et al., "Fluorescence Spectroscopy of Tissue: Recovery of Intrinsic Fluorescence from Measured Fluorescence," Applied Optics, vol. 35, No. 10, pp. 1780-1792 (Apr. 1, 1996).

Graaff et al., "Condensed Monte Carlo Simulations for the Description of Light Transport," Applied Optics, vol. 32, No. 4, pp. 426-434 (Feb. 1, 1993).

Notification of Transmittal of the International Search Report and the Written Opinion of the International Searching Authority, or the Declaration for International Application No. PCT/US2009/041732 (Apr. 15, 2010).

Extended European Search Report for European Patent No. 2001352 (Mar. 5, 2010).

Notice of Allowance and Fee(s) Due for U.S. Appl. No. 11/725,141 (Feb. 22, 2010).

Notice of Allowance and Fee(s) Due for U.S. Appl. No. 11/729,967 (Feb. 19, 2010).

Notice of Allowance and Fee(s) Due for U.S. Appl. No. 11/119,865 (May 1, 2009).

Final Official Action for U.S. Appl. No. 11/119,865 (Mar. 18, 2009).

Communication of European Publication No. And Information on the Application of Article 67(3) EPC for European Patent No. 2005173 (Nov. 26, 2008).

Official Action for U.S. Appl. No. 11/119,865 (Jul. 11, 2008).

Skala et al., "An Investigation of Probe Geometry Designs for the Optical Spectroscopic Diagnosis of Epithelial Pre-Cancers and Cancers," Lasers Surg Med, vol. 34, No. 1, pp. 25-38 (2004).

Pfefer et al., "Selective Detection of Fluorophore Layers in Turbid Media: The Role of Fiber-Optic Probe Design," Optics Letters, vol. 28, Issue 2, pp. 12-122 (Jan. 15, 2003).

Liu et al., "Relationship Between Depth of a Target in a Turbid Medium and Fluorescence Measured by a Variable-Aperture Method," Optics Letters, vol. 27, Issue 2, pp. 104-106 (Jan. 15, 2002).

Non-Final Official Action for U.S. Appl. No. 12/036,717 (Aug. 17, 2010).

Communication pursuant to Article 94(3) EPC for European Patent No. 2001352 (Jul. 13, 2010).

Notice of Allowance and Fee(s) Due for U.S. Appl. No. 11/725,141 (Jun. 11, 2010).

* cited by examiner

METHODS, SYSTEMS, AND COMPUTER PROGRAM PRODUCTS FOR OPTIMIZATION OF PROBES FOR SPECTROSCOPIC MEASUREMENT IN TURBID MEDIA

CROSS REFERENCE TO RELATED APPLICATIONS

This application claims the benefit of U.S. Provisional Patent Application Ser. No. 60/702,228, filed Jul. 25, 2005, the disclosure of which is incorporated herein by reference in its entirety.

GRANT STATEMENT

The presently disclosed subject matter was made with United States Government support under Grant No. CA100599 awarded by the National Institutes of Health. Thus, the United States Government has certain rights in the presently disclosed subject matter.

TECHNICAL FIELD

The presently disclosed subject matter relates to the field of fiber optics. More particularly, the presently disclosed subject matter relates to methods, systems, and computer program products for optimization of probes for spectroscopic measurement in turbid media.

BACKGROUND

Diffuse reflectance spectra, which are indicative of the absorption and scattering properties of cells and/or tissues, are sensitive to a number of important biological molecules. In cells and/or tissues, absorption is due at least in part to the presence of various biological molecules, such as proteins, carotenoids, and hemoglobin, and scattering is attributed inter alia to the size and density of intracellular and extracellular structures. Diffuse reflectance spectroscopy has therefore been investigated as a possible approach to diagnosing early pre-cancerous and cancerous changes in such cells and/or tissues (Thueler et al. (2003) 8 *J Biomed Opt* 495-503; Muller et al. (2001) 40 *Appl Opt* 4633-46; Palmer et al. (2003) 50 *IEEE Trans Biomed Eng* 1233-42; Finlay & Foster (2004) 31 *Med Phys* 1949-59; Georgakoudi et al. (2002) 62 *Cancer Res* 682-687, 2002). However, due to the complex interplay between absorbers and scatterers in cells and/or tissues, it can be difficult to relate a measured diffuse reflectance spectrum to the underlying physical features of the cells and/or tissues.

The illumination/collection geometry of the probe that is employed can be an important aspect of cell/tissue optical spectroscopic measurements in that it can affect sensitivity to the optical properties (absorption and scattering coefficients), sensing volume, and signal to noise (Mourant et al. (1997) 36 *Appl Opt* 5655-5661; Zhu et al. (2003) 8 *J Biomed Opt* 237-247; Pogue & Burke (1998) 37 *Appl Opt* 7429-36). There are numerous possible probe designs to select from for a given biomedical application.

Specialized probe designs have been previously shown to be useful in characterizing tissue properties from fluorescence (Pogue & Burke (1998) 37 *Appl Opt* 7429-36; Pfefer et al. (2004) 42 *Med Biol Eng Comput* 669-73; Pfefer et al. (2005) 10 *J Biomed Opt* 44016; Zhu et al. (2005) 10 *J Biomed Opt* 024032; Quan & Ramanujam (2004) 29 *Opt Lett* 2034-2036) and diffuse reflectance measurements (Mourant et al. (1997) 36 *Appl Opt* 5655-5661; Amelink et al. (2004) 29 *Opt Lett* 1087-1089). For example, Mourant et al. (36 *Appl Opt* 5655-5661, 1997; hereinafter, "Mourant") discloses that at a source-detector separation of approximately 1.7 mm, the diffuse reflectance collected was insensitive to the scattering coefficient.

Thus, the measured diffuse reflectance could be directly related to the absorption coefficient. Mourant further discloses that for a source-detector separation of 1.7 mm, this relationship is valid for absorption coefficients in the range of 0-0.86 $cm^{-1}$ and reduced scattering coefficients in the range of 7-21 $cm^{-1}$. Using this relationship, the authors were able to extract the concentration of Direct Blue dye from a phantom with errors of 20% or less. This method furthermore required no a priori information about the absorbers and scatterers present in the medium.

However, the error for the reported probe is potentially too great to allow the disclosed probe to be employed for sensitive medical applications, and it is not valid for optical properties typical of tissue in the UV-visible wavelength range. Additionally, Mourant does not optimize the geometry of the fiber optic probe, instead simply testing only the operation of probes with a different separation between source and detector fibers. What are needed, then, are methods for testing various parameters of fiber optic probes for spectroscopic measurements that can be used to optimize probe geometries for applications for which enhanced accuracy is important.

To address this need, the presently disclosed subject matter provides methods for optimizing a fiber optic probe geometry for spectroscopic measurement. Such methods are useful for identifying probe geometries that can be employed for measuring optical properties of cells, tissues, or other turbid media.

SUMMARY

The presently disclosed subject matter provides methods, systems, and computer program products for optimizing a probe geometry for spectroscopic measurement in a turbid medium. According to one method, a probe geometry comprising one emitting entity for emitting electromagnetic radiation into a turbid medium and at least one collecting entity for collecting electromagnetic radiation that interacted with the turbid medium is selected. A simulation is performed with inputs of the probe geometry and a plurality of sets of optical property values associated with the turbid medium to generate output comprising optical parameter values measured by the probe geometry for each set of input optical property values. The measured optical parameter values are input to an inversion algorithm to produce corresponding optical properties as output. The produced optical properties are compared with optical properties known to correspond to the measured optical parameter values and a degree of matching between the produced optical properties and the known optical properties is determined. The simulation and inversion steps are repeated for a plurality of additional probe geometries. Each additional probe geometry differs from the previously tested probe geometry in at least one property. The property may be a quantity of collecting entities, a diameter of at least one emitting or collecting entities, a linear distance between the emitting and collecting entities, or combinations thereof. An optimization algorithm is applied at each iteration to select a probe geometry such that the resulting degree of matching will converge to an optimum value. An optimal geometry is selected based on the degree of matching determined for each geometry.

The terms "emitting entity" and "collecting entity" refer to any structures capable of respectively emitting and collecting electromagnetic radiation at wavelengths of interest.

Examples of structures suitable for use as the emitting and collecting entities include optical fibers capable of emitting and collecting light. However, even though the examples below relate to a probe that includes optical fibers, the subject matter described and claimed herein is not limited to optimizing a probe that emits and collects visible wavelengths of electromagnetic radiation. Optimizing a probe that emits and collects any wavelengths of electromagnetic radiation suitable for determining properties of turbid media is intended to be within the scope of the subject matter described herein.

The subject matter described herein for optimization of probes for spectroscopic measurement in turbid media may be implemented using a computer program product comprising computer executable instructions embodied in a computer readable medium. Exemplary computer readable media suitable for implementing the subject matter described herein include chip memory devices, disk memory devices, programmable logic devices, application specific integrated circuits, and downloadable electrical signals. In addition, a computer program product that implements the subject matter described herein may be located on a single device or computing platform or may be distributed across multiple devices or computing platforms.

BRIEF DESCRIPTION OF THE DRAWINGS

Preferred embodiments of the subject matter described herein will now be explained with reference to the accompanying drawings of which.

DETAILED DESCRIPTION

All references cited herein are incorporated herein by reference in their entireties to the extent that they supplement, explain, provide a background for, or teach methodology, techniques, and/or compositions employed herein.

Figure 1:
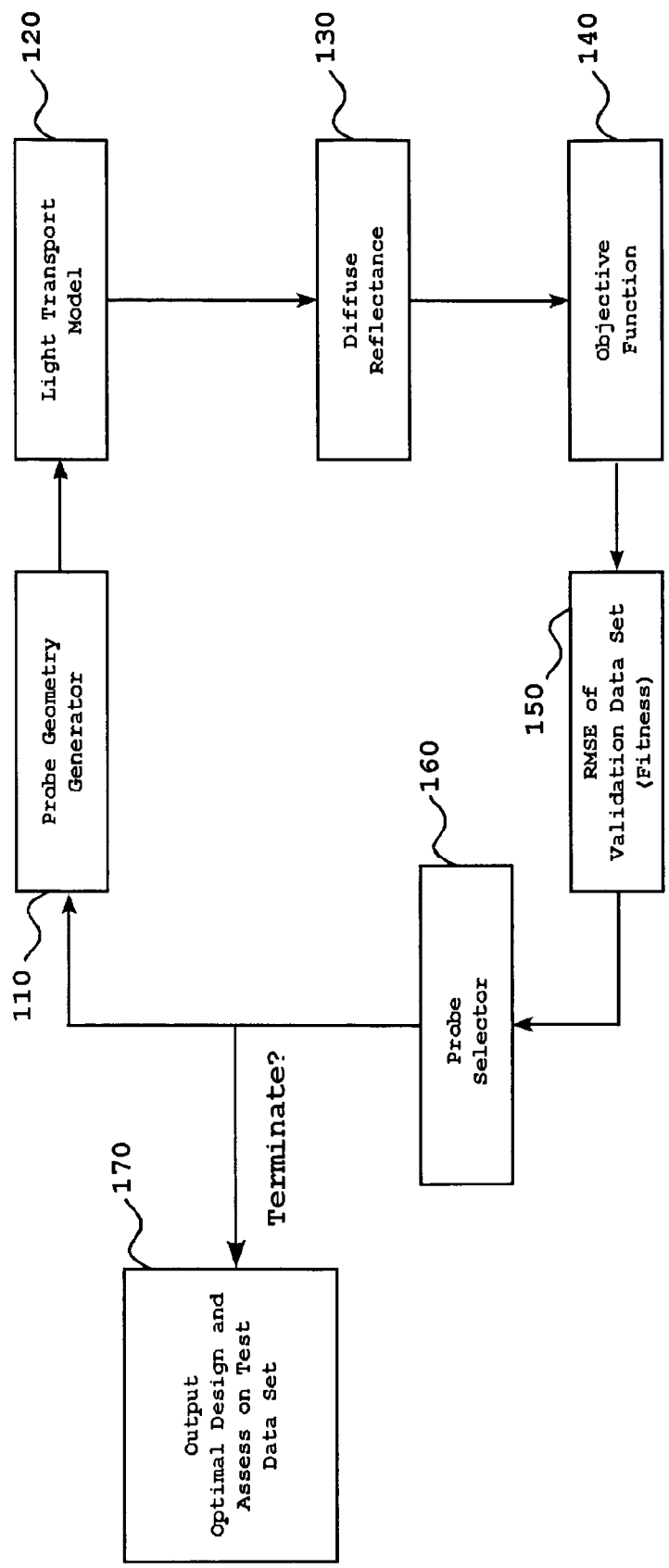
FIG. 1 is a block diagram illustrating exemplary components of a system for optimization of probes for spectroscopic measurement in turbid media according to an embodiment of the subject matter described herein.

FIG. 1 is a block diagram illustrating exemplary components of a system for optimization of probes for spectroscopic measurement in turbid media according to an embodiment of the subject matter described herein. Referring to FIG. 1, the system includes a probe geometry generator 110 for generating a probe geometry to be tested. Probe geometry generator 110 may generate an initial probe geometry including sizes, spacings, and numbers of illumination and collection fibers. The sizes of the fibers may be selected from a group of available fibers sizes (e.g., fibers sizes that are commercially available, including, but not limited to 50 µm, 100 µm, 200 µm, 400 µm, and/or 500 µm). Initial spacings may be selected randomly from increments within bounds defined by the spectroscopic measurement environment. In some embodiments, the initial spacings are limited to a maximum value, and in one implementation, the maximum value is 1.5 mm.

A light transport model 120 may be used to simulate diffuse reflectance properties measured by the probe geometry. In one implementation, light transport model 120 may be implemented using a Monte Carlo simulation model. The output of light transport model 120 for the given probe geometry is diffuse reflectance 130 that would be measured by the probe geometry. In one implementation, ranges of optical properties are input and corresponding diffuse reflectance values are output.

Diffuse reflectance 130 is input to an objective function 140, which takes as input the diffuse reflectance values computed for the different optical properties generated by light transport model 120. The objective function implements an inversion algorithm that determines optical properties corresponding to the diffuse reflectance values produced by light transport model 120 and compares the produced optical properties with optical properties known to correspond to the input diffuse reflectance values. Objective function 140 computes a degree of closeness or matching between the produced optical properties and the known optical properties. In one implementation, the degree of closeness or matching is the root mean squared error (RMSE) 150 between the produced and known optical properties. A probe selector 160 receives the RMSE value for each probe design and selects a probe design that minimizes the RMSE value. Probe selector 160 may apply an optimization algorithm at each iteration to select a probe geometry such that the resulting degree of matching will converge to an optimum value. In one implementation, the optimization algorithm may be a genetic algorithm.

Figure 2:
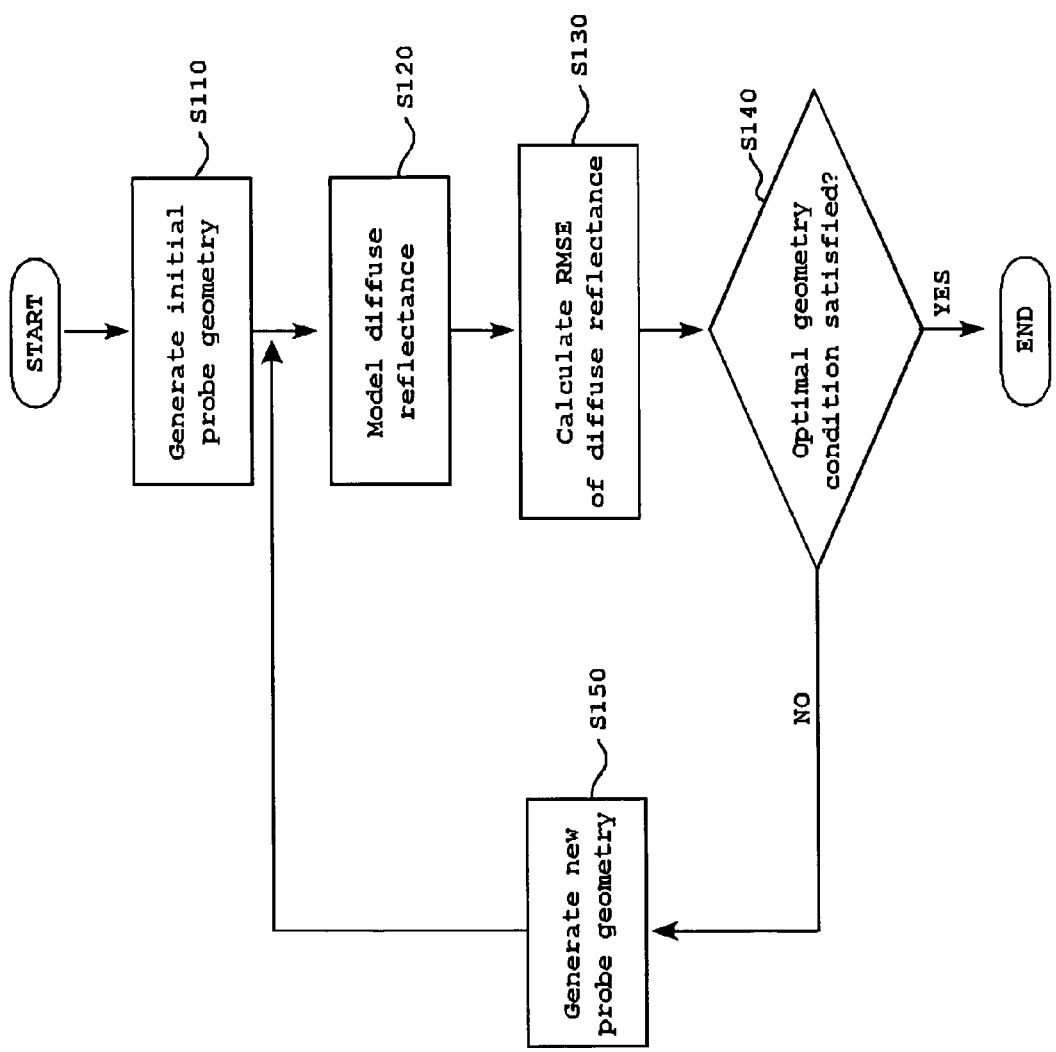
FIG. 2 is a flow chart illustrating an exemplary process for optimization of a probe for spectroscopic measurement in turbid media according to an embodiment of the subject matter described herein.

FIG. 2 is a flow chart illustrating an exemplary process for optimization of a probe for spectroscopic measurement in turbid media according to an embodiment of the subject matter described herein. Referring to FIG. 2, the fiber optic probe optimization method will be described hereinafter. First, at step S110, an initial probe geometry is generated. The initial probe geometry can comprise at least one illumination fiber and at least one collection fiber. In some embodiments, the illumination fiber and the collection fiber are the same fiber, and in some embodiments, the illumination fiber is not a collection fiber.

At step S120, diffuse reflectance is modeled. In order to model diffuse reflectance, a model of light transport that has the ability to quickly and efficiently calculate the diffuse reflectance measured by a given probe geometry for a wide range of optical properties is employed. In some embodiments, a Monte Carlo model of light transport can be used for this purpose.

Next, an appropriate objective function is required to quantitatively evaluate the effectiveness or fitness of a probe having a particular geometry in extracting the optical properties from a turbid medium. In some embodiments, the objective function can employ a neural network algorithm to relate the measured diffuse reflectance to the optical properties of the medium. The neural network can be optimized on a training set and then evaluated on an independent validation set.

At step S130, the root mean square error (RMSE) between the extracted (from the neural network algorithm) and actual optical properties (input into the Monte Carlo simulation) can be output from the objective function to determine the fitness of that particular probe.

At step S140, it is determined whether or not the optimal geometry condition is satisfied. If so, the optimal geometry is outputted, and if not, a new probe geometry is generated at step S150, and steps S110-S140 are iteratively repeated. A genetic optimization algorithm can be used to find the most fit fiber optic probe design, i.e., one that minimizes the RMSE of the optical properties calculated by the objective function, through an adaptive process. The RMSE of the optical properties generated by the objective function using the optimal probe geometry can be evaluated on an independent testing data set. A commercially available genetic algorithm suitable for selecting a probe design that minimizes the RMSE is the GAlib algorithm.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Reflectance Calculation Using a Model of Light Transport

One of the aspects of the optimization process outlined in FIG. 2 is a model of light transport that can generate a diffuse reflectance spectrum for a wide range of optical properties and probe geometries. In some optical property and fiber geometry regimes, the diffusion equation could be used. However, since with regard to reflectance in the UV-VIS range, where tissue is highly absorbing, this method is unsuitable. Therefore, Monte Carlo modeling was used to compute the diffuse reflectance for a given probe geometry. Monte Carlo simulations with point source geometries were used, so that any arbitrary probe geometry could be modeled using convolution.

In addition, the scaling procedures described by Graaff et al. (32 *Appl Opt* 426-34, 1993) were used to scale the output of a single Monte Carlo simulation for any set of optical properties as disclosed in Palmer & Ramanujam (2006) 45 *Appl Opt* 1062-1071. Briefly, the method comprised running a single simulation for a given set of absorption ($\mu_{a,sim}$) and scattering ($\mu_{s,sim}$) coefficients and recording the exit weight ($W_{exit,sim}$), net distance traveled ($r_{t,sim}$), and total number of interactions for each photon (N) that exits the tissue surface. The scaling method then used these stored parameters to calculate the new exit weight ($W_{exit,new}$) [Eq. (1)] and net distance traveled ($r_{t,new}$) [Eq. (2)] for a given photon that had a different absorption ($\mu_{a,new}$) and scattering coefficient ($\mu_{s,new}$) used in the same simulation. The scaling relationships were:

$$W_{exit,new} = W_{exit,sim}\left(\frac{\mu_{s,new}}{\mu_{s,new}+\mu_{a,new}}\right)^N \frac{\mu_{s,sim}+\mu_{a,sim}}{\mu_{s,sim}} \quad (1)$$

$$r_{t,new} = r_{t,sim}\left(\frac{\mu_{s,sim}+\mu_{a,sim}}{\mu_{s,new}+\mu_{a,new}}\right) \quad (2)$$

To further simplify the scaling process, it was assumed that, for a given value of the reduced scattering coefficient, $\mu_s' = \mu_s(1-g)$, the diffuse reflectance would be the same for any values of $\mu_s$ and anisotropy factor (g) that generate the same $\mu_s'$. This has been shown to be valid over the range of g values present in human tissue (i.e., for g values greater than 0.8; Graaff et al. (32 *Appl Opt* 426-34, 1993); Kienle & Patterson (41 *Phys Med Biol* 2221-2227, 1996)). By use of this similarity relation and the scaling procedure outlined hereinabove, only a single Monte Carlo simulation needed to be run to determine the output of a Monte Carlo simulation for any set of optical properties. The Henyey-Greenstein phase function was used in the single Monte Carlo simulation as described hereinbelow.

Convolution was used to integrate over the illumination and collection fibers to determine the probability that a photon, traveling a fixed distance, would be collected for a given probe geometry. This takes advantage of the spatial invariance and rotational symmetry present in a homogeneous medium. For a pair of illumination and collection fibers, the probability of collection of a photon traveling a net distance $r_t$ between the points of entering and exiting the medium is given by:

$$\frac{1}{\pi^2 r_i^2} \int_{max(-r_i,s-r_t-r_c)}^{min(r_i,s-r_t+r_c)} (s-x) \quad (3)$$

$$\cos^{-1}\left[\frac{s^2+(s-x)^2-r_i^2}{2(s-x)s}\right] \times \cos^{-1}\left[\frac{r_t^2+(s-x)^2-r_i^2}{2(s-x)r_t}\right] dx$$

where $r_i$ is the radius of the illumination fiber, $r_c$ is the radius of the collection fiber, s is the separation between the centers of the illumination and the collection fibers, and x is the spatial variable over which the integral is taken (see appendix for derivation). This equation was numerically integrated. To adapt this to the fiber bundle used in this study (the geometry of the fiber bundle is described below), the common end of the fiber bundle was imaged, and the centers of each illumination and collection fiber in the bundle were determined. Then the probe geometry was integrated pairwise (for each illumination-collection fiber pair) to determine the total probability of collection. It was found that imaging the fiber bundle to obtain the exact location of each illumination and collection fiber was necessary. Approximating the fiber bundle as solid rings of illumination and collection fibers produced significant errors in the model, likely because of imperfect physical placement of the fibers within the bundle.

It was found that the scaling process and subsequent numerical integration for the probe geometry of a large number of photons required approximately 1 s to complete, which, although much faster than running an independent simulation, was still rather slow for performing an inversion procedure. Therefore, the diffuse reflectance values for a range of optical properties $\mu_s$, 5-500 cm$^{-1}$; $\mu_a$, 0-200 cm$^{-1}$; g, 0.8) were determined ahead of time to form a lookup table, and cubic splines were used to interpolate between table values. The smallest increment used in the lookup table was 0.1 cm$^{-1}$ for $\mu_a$ and 2.5 cm$^{-1}$ for $\mu_s$. This allowed for rapid determination of the diffuse reflectance for a given fiber probe geometry and a wide range of optical properties, without requiring independent Monte Carlo simulations.

Three simulated data sets were generated using Monte Carlo simulations: training, validation, and testing data sets. The training data set was used to train the neural network algorithm to extract optical properties from diffuse reflectance measurements with a particular probe geometry over a wide range of optical properties. The validation and testing data sets were used in two different stages of the optimization process. The validation data set was used in each iteration of the optimization loop shown in FIG. 2, to evaluate the fitness of a given probe geometry with an independent set of optical properties (which were not used in training the algorithm). The RMSE calculated from the results of the validation data set was used as the measure of probe fitness. The optimal probe design selected by the genetic algorithm at the end of the iterative process was applied to the testing data set. The output of the testing data set was used to determine the accuracy with which the optimal probe design could extract optical properties from an independent data set in an unbiased manner.

Training Data Set. A single Monte Carlo simulation, consisting of $55 \times 10^6$ photons, having the following properties: absorption coefficient ($\mu_a$): 0, scattering coefficient ($\mu_s$): 150 cm$^{-1}$, anisotropy factor (g): 0.8, was first simulated. The refractive indexes were chosen to be 1.4 for the medium, which is representative of a number of tissue types (Bolin et al. (1989) 28 *Appl Opt* 2297-2303), and 1.47 for the fiber (representative of fused silica) above this medium. The medium was semi-infinite and homogeneous. The simulation was run using a point-source geometry and photons were collected at the surface. The scaling procedures described by Graaff et al. (32 *Appl Opt* 426-34, 1993) were used to adjust the simulation to any desired set of optical properties. Convolution was used to account for the specific fiber probe geometries evaluated in the optimization process. The Quasi-Discrete Hankel Transform, described by Li et al. (23 *Opt Lett* 409-11, 1998) was used to perform the convolution.

The training data set consisted of 144 sets of optical properties. The total attenuation coefficient $\mu_t$ (defined as $\mu_a + \mu_s$) ranged from 25 to 200 cm$^{-1}$. At each $\mu_t$, the albedo (defined as $\mu_s/\mu_t$) ranged from 0.6 to 1, with g fixed at 0.8. This corresponds to a range of $\mu_a$ from 0 to 80 cm$^{-1}$ and reduced scattering coefficient $\mu_s'$ (defined as $\mu_s \times (1-g)$) from 3 to 40 cm$^{-1}$. This set of optical properties encompasses that found in a number of tissue types in the UV-VIS spectral range (see Cheong (1995) in *Optical-Thermal Response of Laser-Irradiated Tissue, Lasers, Photonics, and Electro-optics* (Welch & Gemert (eds)), Plenum Press, New York, N.Y., United States of America, pp. 275-303), and is consistent with findings of the optical properties in human breast tissue reported by the co-inventors (Palmer et al. (2006) 45 *Appl Opt* 1072-1078). $\mu_t$ was assigned because for a given fixed $\mu_t$, the spatial scaling of the Monte Carlo simulation to accommodate the desired set of optical properties is fixed. This leads to an increase in the efficiency of the Hankel transform by allowing much of the computational load involved in calculating the Hankel transform to be conserved (Li et al. (23 *Opt Lett* 409-11, 1998) refers to this as the "C" matrix, which needs only be calculated once in this case). The output is the modeled diffuse reflectance for a wide range of optical properties, calculated for the specific fiber geometry being evaluated.

Validation/Testing Data Set. The validation and testing data sets both consisted of 25 randomly assigned sets of optical properties (chosen from within the range specified for the training data set). The anisotropy factor, g, was also randomly chosen within the range of 0.8 to 0.95, while scaling $\mu_s$ to keep $\mu_s'$ within the same range used in the training data set. Independent Monte Carlo simulations were run for the 25 sets of optical properties with 10e6 photons used in the validation and testing data sets and convolution was again used to model a specific probe geometry. As stated above, the validation data set was used in each iteration of the optimization loop to evaluate fitness of a probe geometry to a set of optical properties. The testing data set was used to test the probe geometry selected using the genetic algorithm for its ability to extract optical properties.

Example 2

Objective Function

Once the diffuse reflectance for a probe geometry has been modeled using the light transport model, the next phase of the optimization flow chart shown in FIG. 2 is the objective function. In order to extract the optical properties of the medium from its diffuse reflectance, a neural network objective function was used to determine the optical properties based on the diffuse reflectance collected for a given probe geometry. A neural network objective function was chosen because it is useful in approximating complex non-linear functions and has previously been shown effective in extracting optical properties (Pfefer et al. (2003) 8 *J Biomed Opt* 206-215). This works on the principle that the spatial distribution and intensity of the diffusely reflected light can be determined by the optical properties of the medium, under the assumption that given enough sampling points (in this case collection fibers), these optical properties can be uniquely determined.

The neural network employed consisted of 10 neurons having hyperbolic tangent activation functions, and two output neurons (corresponding to $\mu_a$ and $\mu_s'$) having linear activation functions. The neural network was trained using the Monte Carlo generated training data set described hereinabove using a Levenberg-Marquardt algorithm in MATLAB® (Mathworks Inc., Natick, Mass., United States of America).

Briefly, the neural network works as an interconnected assembly of simple processing units. The neurons themselves are fixed as simple functions (in this case hyperbolic tangent or linear functions). The network is adaptable by weighting the connections from one neuron to the next: i.e., the output of one neuron is the input to another neuron, modulated by a particular weight. The universal approximation theorem states that in using a neural network with only a single hidden layer (such as the one employed herein—having one layer of neurons between the input and output neuron layers), any continuous function can be approximated with arbitrary precision (Chen & Chen (1993) 4 *IEEE Trans Neural Networks* 910-918). This thus represents a powerful tool for approximating complex, non-linear relationships where analytical solutions are not possible.

Upon training the neural network for a given fiber geometry, the fitness of that individual fiber geometry was quantified by the RMSE of the extracted optical properties from the 25 independent simulations in the validation set. The RMSE was calculated separately for absorption and reduced scattering coefficients ($\mu_a$ and $\mu_s'$, respectively). The RMSE for the absorption coefficient and the RMSE for the reduced scattering coefficient were then summed, and this value was used to characterize the fitness of the particular probe fiber geometry. This procedure allowed for selection of a fiber geometry that performs well not only on the training data set, but which also generalizes well to a set of independent simulations.

Example 3

Optimization with Genetic Algorithm

The goal of the genetic algorithm was to minimize the returned fitness score of a given fiber geometry, thereby reducing the error with which the optical properties can be extracted. Genetic algorithms represent a robust means of optimization and have advantages over commonly used gradient techniques in that they are less sensitive to the initial guess and perform well in regions of small gradients or discontinuities (see e.g., Eiben & Smith (2003) *Introduction to Evolutionary Computing*, New York, N.Y., United States of America, Springer-Verlag).

Genetic algorithms have been effectively employed in optimization applications. For example, they have been used successfully in optimizing the microstructure of communications fibers to maximize throughput (Manos & Poladian (2004) 21 *Eng Comput* (Swansea, Wales) 564-576). As opposed to gradient methods, which take an initial guess and attempt to move it in a direction that leads to a better solution, genetic algorithms work with a population of solutions. Operators similar to those of natural evolution, such as crossover, mutation, and selection are employed to produce offspring and evolve the population of solutions toward an optimal solution.

In generating a new solution, two "parent" solutions were selected from which a new "child" solution was derived. "Crossover" refers to the blending of the two parent solutions to form a child solution (e.g., the illumination fiber diameter of the child solution might be chosen to be the same as the diameter of one of the parent solutions). Random mutation introduced random variability into the child solution (e.g., by randomly altering the source-detector separation), to introduce greater diversity into the resulting solution set. The specific guidelines by which these operators were applied are described in the following section.

The population of solutions was updated in steps known as generations. At each generation a population of child solutions was generated from the parent population. Parent individuals for the next generation of child solutions were chosen based on the process of selection. Selection was weighted towards the fittest individuals (i.e., fitter individuals are more likely to be chosen as parents), thereby introducing selective pressure on the population to evolve towards an optimal solution.

Variable Fiber Parameters. The GAlib genetic optimization library (Wall (2005) "GAlib: Matthew Wall's Genetic Algorithm Library," vol. 2005) was used to optimize the fiber design parameters. A number of adjustable fiber parameters are possible. These include the numerical aperture (NA), fiber diameter, and number and location of the illumination and collection fibers. It is also possible to use angled fibers to alter the direction of photon propagation, and so affect the probing volume (Quan & Ramanujam (2004) 29 *Opt Lett* 2034-2036). In order to simplify the modeling, only the diameter and source-detector separations were included as free parameters.

Two basic probe designs were tested. In the first case, the probe consisted of a single illumination fiber, and between two and six collection fibers (a total of five possible configurations). In the second case, there was similarly a single illumination fiber, but it was also used for collection of light. There were additional fibers (between one and five) that served to collect light only (another 5 possible configurations). Thus, each of the basic probe designs had between two and six independent channels of light collection, for a total of ten configurations.

A series of optimizations employing the methodology shown in FIG. 2 was run to consider each of the ten probe configurations separately. This approach allowed for a comparison of the cases where overlapping and non-overlapping source-detector geometries were used and also permitted an evaluation of additional design complexity by adding additional channels of light collection.

The illumination fiber had a variable diameter, having possible values of 50, 100, 150, 200, 300, 400, and 500 $\mu$m. These properties corresponded to commercially available fibers. The remaining collection fibers also had a variable fiber diameter, as well as a variable center-to-center distance from the source fiber. The possible diameters consisted of the same set of diameters used for the source fiber, while the source-detector separation was limited to less than 1.5 mm, and greater than the sum of the source and collection fiber radii (cladding included). All fibers had a numerical aperture (NA) of 0.22 and specular reflection was not collected.

Genetic optimization parameters. First, a set of 25 fiber optic probe solutions was randomly initialized within the set of possible solutions outlined above, to form the initial population of solutions. From this set pairs of two at a time were randomly selected. Next, a child solution was generated, which exhibited a mixture of the characteristics of the selected parent solutions. For the fiber diameter, the diameter of the offspring was selected randomly from either of the two parents. For the source-detector separation distance, a blending algorithm (Wall (2005) "GAlib: Matthew Wall's Genetic Algorithm Library," vol. 2005) was chosen such that the separation distance was randomly selected from a region centered at the mean of the two parent separation distances, and having a range of twice the difference between the two parent separations. Crossover was performed with a probability of 0.9 for each new individual. In cases where it was not performed, the child solution was identical to one of the parents.

In addition to the crossover operator, a random mutation operator was also employed to introduce greater diversity into the population. This was done after a child solution was generated, and when mutation occurred, the mutated solution took the place of the original child solution. For the fiber size, a new size was randomly selected from the allowed set (commercially available fiber sizes). For the separation distance, a random Gaussian number with a standard deviation of 0.3 mm was added to the separation of the fiber. The random mutation was applied with a probability of 0.005 for each variable. For all operators, the bounds of the variables, as described above, were respected. The probabilities at which the crossover and mutation operators were applied were chosen based on commonly used values in the literature.

Finally, the roulette method of selection (Eiben & Smith (2003) *Introduction to Evolutionary Computing*, Springer-Verlag, New York, N.Y., United States of America) was employed to select offspring that make up the next generation, weighted towards the most fit individuals. This method was analogous to spinning a roulette wheel, where larger sections of the wheel were devoted to the fittest individuals. In other words, the fittest individuals had a higher probability of being selected as parents for the next generation. This was the mechanism that drove the population of solutions towards the optimum. A total of 500 generations were run with the best individual taken as the final solution.

After termination of the optimization loop, the optimal fiber geometry was output by the algorithm. The neural network algorithm incorporating the optimal probe geometry was applied to a testing data set in order to provide an unbiased estimate of the effectiveness of a given fiber geometry/neural network algorithm for extracting optical properties from the diffuse reflectance signal.

Example 4

Phantom Validation

The approach disclosed herein was experimentally validated by constructing a fiber optic probe according to the specifications for the optimal probe provided by the optimization algorithm and using it to acquire diffuse reflectance measurements from tissue phantoms that have optical properties that fall within the range used in the simulation studies. The constructed probe consisted of a single source fiber and two separate collection fibers (which was found to have the best performance in the simulation studies). The tip of the probe was imaged to determine the fiber sizes and their positions relative to each other, and the neural network algorithm was trained using a training data set of Monte Carlo simulations for the exact probe geometry at the tip of the constructed fiber probe.

The probe was coupled to a custom built spectrometer, consisting of a 450-W xenon lamp (FL-1039, HORIBA Jobin Yvon Inc., Edison, N.J., United States of America), a scanning double-excitation monochromator (Gemini 180, HORIBA Jobin Yvon Inc.), an imaging spectrograph (IHR320, HORIBA Jobin Yvon Inc.), and a CCD camera (Symphony, HORIBA Jobin Yvon Inc.). All measurements were conducted with the excitation monochromator passing zero order white light, with slits at 1 mm. The imaging spectrograph was set to have a center wavelength of 485 nm, corresponding to a range of 353-616 nm. The entrance slit to the imaging spectrograph was set to 0.4 mm, corresponding to a full-width half maximum bandpass of 3.76 nm. Integration times ranged from 40 ms to 3 s.

A set of liquid homogeneous phantoms was then created. The phantoms contained variable concentrations of hemoglobin (absorber) and polystyrene spheres (scatterer). First, three solutions with variable volume densities of polystyrene spheres (07310-15, Polysciences, Inc., Warrington, Pa., United States of America) suspended in water were made to produce three phantoms with different scattering coefficients. To each of these base phantoms, 3 titrations of hemoglobin (H7379-16, Sigma Co., St. Louis, Mo., United States of America) solution were added to produce three different absorption coefficients, with a diffuse reflectance measurement made after each addition. This produced a set of 9 phantoms with a range of absorption and scattering properties. All measurements were conducted the day the phantoms were made.

The wavelength dependent extinction coefficients for hemoglobin were measured using an absorption spectrophotometer (Cary 300, Varian, Inc., Palo Alto, Calif., United States of America). It was assumed that the oxygenation of hemoglobin was constant through the course of the experiment. The reduced scattering coefficient was determined from Mie theory using freely available software (Prahl (2003) "Mie Scattering Program", vol. 2003: Oregon Medical Laser Center), given the known size (1 μm), density, and refractive index of the spheres (1.60) and the surrounding medium, water (1.33). The refractive index of polystyrene spheres has been reported to be constant to within approximately 1% of this value over the wavelength range used (Xiaoyan et al. (2003) 48 *Phys Med Bio* 4165-4172). Tables 1 and 2 show the means and ranges of $\mu_s'$ and $\mu_a$, respectively, for each absorption and scattering level over the wavelength range of 353-617 nm. All combinations of these absorption and scattering levels were measured with the fiber-optic probe and spectrometer. The range of optical properties represents a subset of those used in the simulation studies, but still cover a range of optical properties representative of those found in the human breast and other tissues (Palmer et al. (2006) 45 *Appl Opt* 1072-1078).

TABLE 1

Reduced Scattering Coefficients for Each of Three Concentrations of Polystyrene Spheres Employed in Phantom Experiments

| Phantom | Mean $\mu_s'$ (cm$^{-1}$) | $\mu_s'$ range (cm$^{-1}$) |
|---|---|---|
| $\mu_s'$ level 1 | 6.1 | 5.5-6.9 |
| $\mu_s'$ level 2 | 16 | 14-18 |
| $\mu_s'$ level 3 | 24 | 22-28 |

TABLE 2

Absorption Coefficients for Each of Three Concentrations of Hemoglobin Employed in Phantom Experiments

| Phantom | Mean $\mu_a$ (cm$^{-1}$) | $\mu_a$ range (cm$^{-1}$) |
|---|---|---|
| $\mu_a$ level 1 | 1.3 | 0.35-6.0 |
| $\mu_a$ level 2 | 2.6 | 0.69-12 |
| $\mu_a$ level 3 | 5.0 | 1.3-23 |

To correct for the instrument response, and the difference in magnitude between the Monte Carlo simulations (which are on an absolute scale) and those of the phantoms (which are on a relative scale) a single phantom with known optical properties was used as a reference. The ratio of the simulated spectrum, given the known optical properties of this phantom, and its measured spectrum was taken. All experimental data was multiplied wavelength by wavelength by this calibration ratio.

Table 3 shows the RMSE in $\mu_a$ and $\mu_s'$ selected from the testing data sets for the optimal probe configuration from each of the ten basic fiber probe configurations. The optimal probe geometries are also listed. It can be seen that as the number of fibers increased beyond two collection fibers, the RMSE of the testing data set did not decrease. This indicated that two collection fibers were sufficient for extraction of the optical properties, and the use of additional fibers led to over-training of the algorithm. Fiber probe configurations with additional fibers (greater than 5 collection channels) were not considered for this reason.

TABLE 3

Root Mean Square Errors (RMSE) in $\mu_a$ and $\mu_s'$ from Testing Data Sets for the Optimal Probe Configuration
Selected from Each of Ten Basic Fiber Probe Configurations*

| Fiber design | RMSE - testing (cm$^{-1}$) $\mu_a$ | RMSE - testing (cm$^{-1}$) $\mu_s'$ | Illumination Diameter (μm) | Optimal Geometry Diameter - Source Detector Separation Pairs for Each Collection Fiber (μm) |
|---|---|---|---|---|
| 3 total fibers, no collection by source fiber | 0.41 | 0.30 | 500 | (200-380) (400-1360) |
| 4 total fibers, no collection by source fiber | 0.47 | 0.32 | 200 | (200-610) (500-1330) (500-440) |
| 5 total fibers, no collection by source fiber | 0.46 | 0.34 | 400 | (50-550) (400-530) (50-1180) (300-1230) |
| 6 total fibers, no collection by source fiber | 0.40 | 0.29 | 400 | (200-640) (300-1120) (400-490) (500-1190) (50-700) |
| 2 total fibers, collection by source fiber | 0.48 | 0.81 | 500 | (500-1490) |
| 3 total fibers, collection by source fiber | 0.49 | 2.30 | 500 | (150-1430) (150-1370) |
| 4 total fibers, collection by source fiber | 1.07 | 1.09 | 500 | (100-1390) (50-1270) (100-1250) |
| 5 total fibers, collection by source fiber | 0.50 | 0.89 | 500 | (100-1200) (50-1220) (400-1130) (500-1320) |

*The optimal probe geometry is also provided, showing the diameter of the illumination fiber, with the collection fiber diameter and source detector separation pairs for each of the collection fibers - listed as (diameter - separation) for each fiber.

In addition, the probe configurations where the source fiber was not used for collection outperformed the case where it was. The fiber design that performed the best was the case where there were 3 total fibers, and the source fiber was not used for collection. This fiber design provided the best balance between maximizing performance and minimizing probe complexity.

Figure 3:
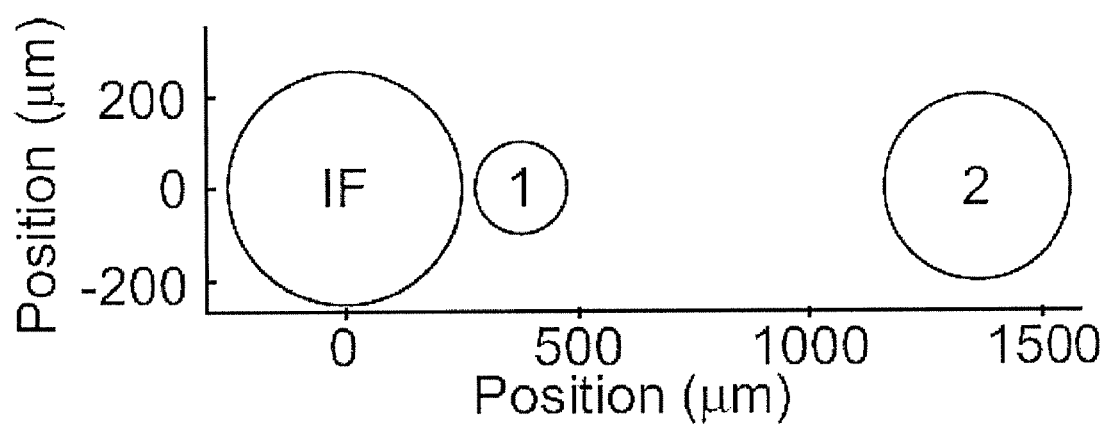
FIG. 3 depicts an optimized fiber design showing illumination fiber(IF) and collection fibers 1 and 2.

FIG. 3 shows the optimal fiber probe geometry. It consisted of a single 500 μm diameter illumination fiber, a 200 μm diameter collection fiber at a center-to-center distance of 380 μm, and a second 400 μm diameter collection fiber at a center-to-center distance of 1360 μm. In FIG. 3, solid areas indicate fiber dimensions to scale. This is design comprises 3 total fibers where the illumination fiber is not used for collection.

Figure 4:
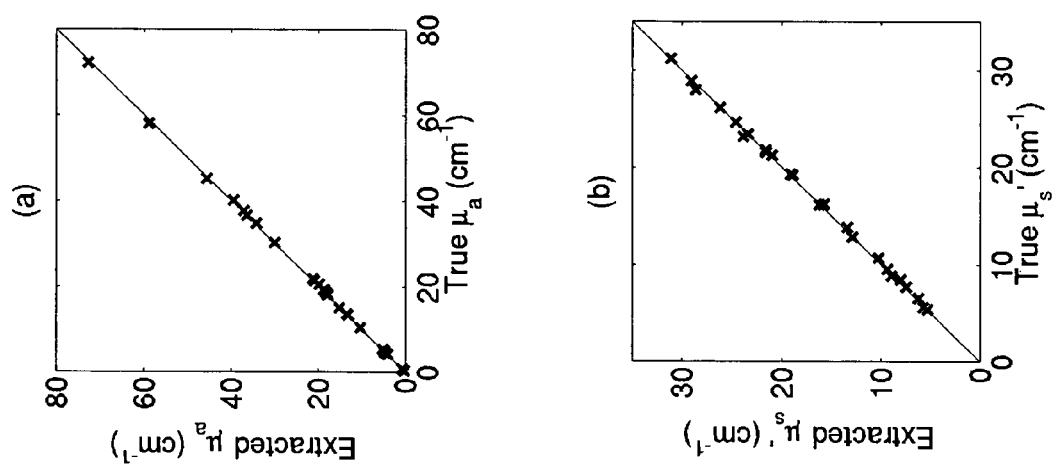
FIGS. 4A and 4B are scatter plots of the extracted vs. expected absorption coefficient (FIG. 4A) and reduced scattering coefficient (FIG. 4B)

FIG. 4 shows a scatter plot of the extracted vs. expected optical properties obtained from the testing data set for the probe design shown in FIG. 3. The solid lines in FIGS. 4A and 4B depict the line of perfect agreement. These results are for the fiber design with 3 total fibers where the illumination fiber is not used for collection. It can be seen that the extracted optical properties showed minimal deviation from the expected optical properties over the entire range tested for both $\mu_a$ (FIG. 4A) and $\mu_s'$ (FIG. 4B). The optical properties were extracted with an RMSE of 0.41 cm$^{-1}$ for $\mu_a$, (tested range of 0-80 cm$^{-1}$) and 0.30 cm$^{-1}$ for $\mu_s'$ (tested range of 3-40 cm$^{-1}$) using the simulated data.

Next, because practical implementation of this probe design would introduce some variability into the positioning of the fibers, the sensitivity of the RMSE to positioning error was evaluated. To evaluate the effects of a wide range of positioning errors, two random numbers were generated following a Gaussian distribution with a mean of zero and a variable standard deviation to evaluate a range of design tolerances. The optimal fiber design described above was altered by adding these numbers to the two source detector separations (both separations were thus randomly altered at the same time). The minimum separation was fixed such that the fibers would not overlap. The neural network was then trained on diffuse reflectance generated for the resulting probe geometry (that which includes the positioning errors), and evaluated with an independent testing data set for the same probe geometry. The positional errors were incorporated into both the training and testing data sets because in practical implementation, the fiber probe would be in direct contact with the tissue surface, with no shield or casing covering the fibers themselves, thus allowing the tip of each fiber to easily be imaged using a reflected light microscope. Any positional errors in the practical probe geometry can thus be easily incorporated into the model, as was done here.

The process was repeated 5 times (using 5 different sets of random numbers selected from the Gaussian distribution) to evaluate the variability of the error with different random perturbations of the fiber positions. Next, the mean and standard deviations of the RMSE were calculated.

Table 4 shows the results of the sensitivity analysis on fiber positioning error. It can be seen that for the case where the positioning error had a standard deviation of 50 μm, the RMSE was identical to those obtained when the source detector separations was exactly defined. As the positioning error increased, the RMSE also increased, with the error in $\mu_s'$ increasing more rapidly than that of $\mu_a$. It also was determined that small changes in the fiber diameters did not greatly impact the accuracy with which the optical properties could be extracted, although this would likely not be as much of a concern in practice since the fiber diameters are well defined.

TABLE 4

RMSE of Extracted Optical Properties vs. Positioning Errors

| Fiber Positioning Standard Deviation (μm) | Mean RMSE (cm$^{-1}$) $\mu_a$ | Mean RMSE (cm$^{-1}$) $\mu_s'$ |
|---|---|---|
| 0 | 0.41 | 0.30 |
| 50 | 0.41 ± 0.01 | 0.30 ± 0.02 |
| 100 | 0.43 ± 0.01 | 0.36 ± 0.06 |
| 200 | 0.46 ± 0.07 | 0.55 ± 0.35 |
| 500 | 0.51 ± 0.11 | 0.94 ± 0.70 |

Figure 5A:
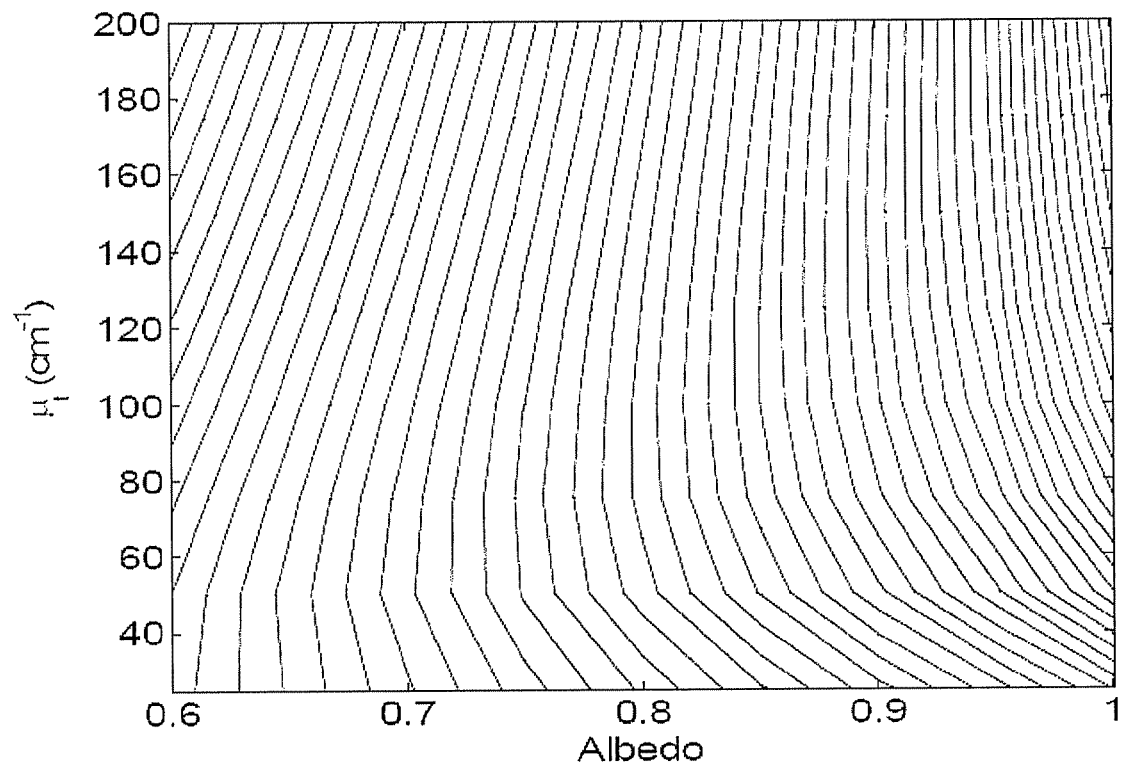
FIGS. 5A and 5B are log contour plots of the collected diffuse reflectance from fiber 1 (FIG. 5A) and fiber 2 (FIG. 5B)
Figure 5B:
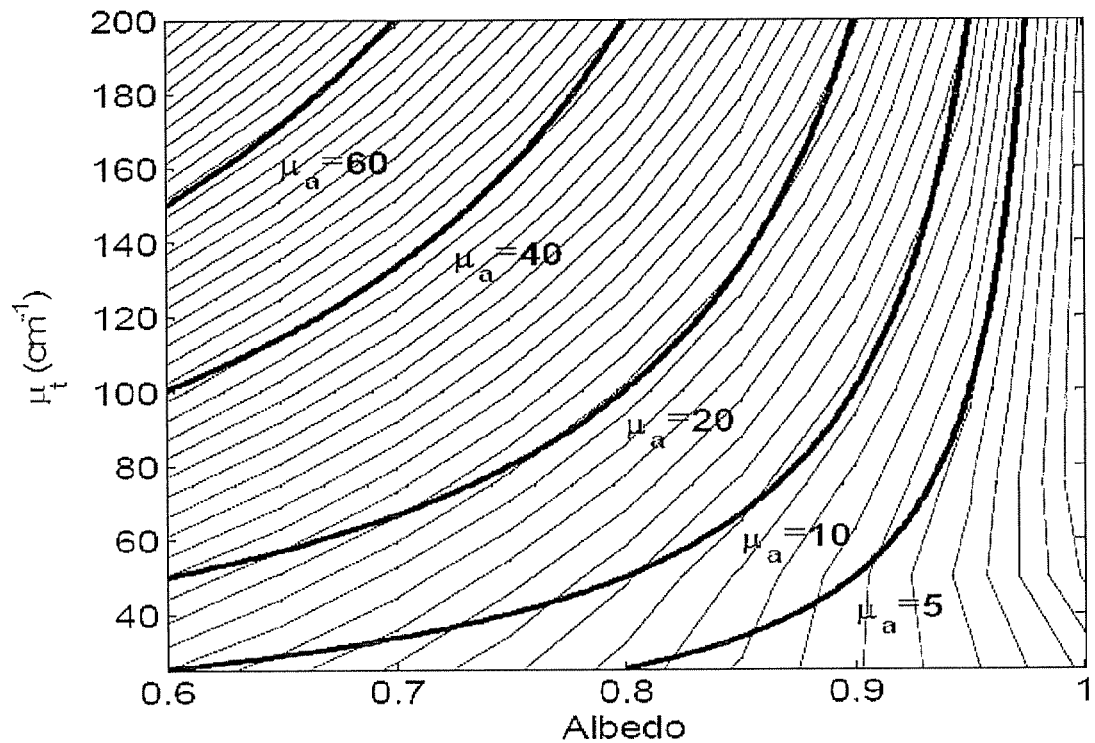

It is desirable to gain some understanding as to why this particular fiber design performs well. FIG. 5 shows a log scale contour plot of the collected diffuse reflectance as a function of $\mu_t$ and albedo for each of the two collection fibers (illustrated in FIG. 3). The plots show that the contour lines in FIG. 5A roughly follow the vertical lines of equal albedo, while the contour lines in FIG. 5B roughly follow the lines of equal $\mu_a$ (bold lines). It can be seen in FIG. 5A that the contour plot of the diffuse reflectance collected from fiber 1 had roughly vertical contour lines. This indicated that for a given albedo (or fixed proportion of $\mu_s$ and $\mu_t$), the reflectance collected by this fiber was relatively insensitive to changes in $\mu_t$.

On the other hand, for collection fiber 2 (FIG. 5B), the contour lines roughly followed the lines of constant $\mu_a$, which are shown as thick black lines. This indicated that for a given fixed absorption coefficient, the diffuse reflectance was relatively insensitive to changes in scattering. As a result, the diffuse reflectance collected by fiber 1 gave a direct measure of the albedo and the diffuse reflectance collected by fiber 2 gave a direct measure of the absorption coefficient. The scattering coefficient could be determined directly from these two parameters. Note that these relationships appeared to break down somewhat at low values of $\mu_t$, and in this case the extraction of optical properties would become on a more non-linear function of the collected reflectance from each fiber, all of which was handled by the neural network function.

Figure 6:
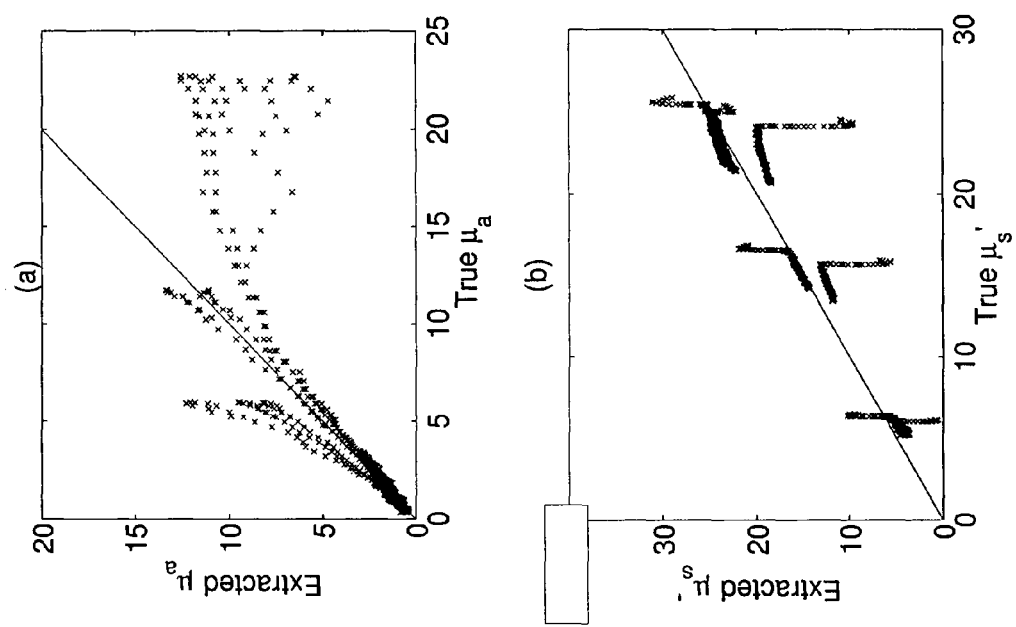
FIGS. 6A and 6B are scatter plots of the extracted vs. true optical properties for experimental studies over the wavelength range 400-616 nm for the absorption coefficient (FIG. 6A) and for the reduced scattering coefficient (FIG. 6B)

Next, this approach was experimentally validated. A probe was constructed meeting the design specifications shown in FIG. 3 and it was used to measure diffuse reflectance from a series of phantoms with a wide range of optical properties. The neural network algorithm was trained using a Monte Carlo training data set as before using the exact fiber configuration in the actual probe, but was tested on experimental measurements made with that probe. FIG. 6 shows the extracted vs. true $\mu_a$ (FIG. 6A) and $\mu_s'$ (FIG. 6B) for the set of phantoms with optical property ranges in Tables 1-2. These data were obtained using the phantom with scattering level 2 and absorption level 2 as the reference phantom, with all other phantoms used to test the algorithm.

The data from 400-616 nm are shown. Wavelengths shorter than 400 nm were excluded due to poor signal to noise owing to the poor efficiency of the charge coupled device (CCD) and lower lamp output at these wavelengths. It can be seen that the accuracy of the method was somewhat less than that obtained with simulation, which was not unexpected, but the performance degraded particularly for high $\mu_a$. The RMSE for the data shown in FIG. 5 was 2.0 cm$^{-1}$ and 2.3 cm$^{-1}$ for $\mu_a$ and $\mu_s'$, respectively. Repeating this for all possible reference phantoms, and averaging the RMSE yields mean RMSEs of 2.4±0.5 cm$^{-1}$ and 3.7±1.4 cm$^{-1}$ for $\mu_a$ and $\mu_s'$, respectively. These phantoms had a range of 0.35-23 cm$^{-1}$ and 5.2-26 cm$^{-1}$ for $\mu_a$ and $\mu_s'$, respectively, over this wavelength range.

Figure 7:
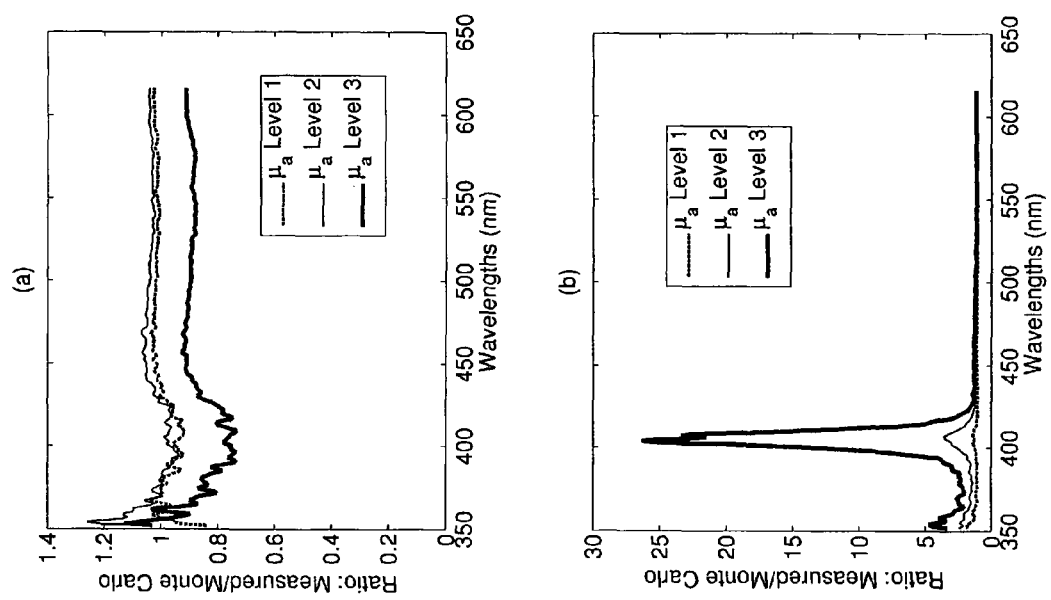
FIGS. 7A and 7B are plots depicting the ratio of the measured to simulated diffuse reflectance spectra at the smaller (FIG. 7A) and larger (FIG. 7B) source detector separations for phantoms with scattering level 2.

The sources of error in the experimental results were evaluated by comparing the simulated and diffuse reflectance measurements at the two different source-detector separations in the probe geometry. FIG. 7 shows the ratio of the measured and simulated diffuse reflectance for the shorter (FIG. 7A) and larger (FIG. 7B) source-detector separations for the three phantoms with scattering level two. Only a subset of the phantoms is shown to make the plot easier to interpret, however similar trends are seen in phantoms at the other two scattering levels.

For this plot a solution of polystyrene spheres of the same concentration was used as a calibration standard to correct for the wavelength dependent response of the system (i.e., the ratios were normalized wavelength by wavelength to that of the calibration standard). A phantom with no absorber added was chosen as the reference in this case to exclude errors associated with absorption effects from the reference phantom, which tends to cancel out errors seen in the highly absorbing phantoms, and introduce artifacts into the minimally absorbing phantoms. Were the experimental and simulated data in perfect agreement, there would be a ratio of 1 across all wavelengths. It can be seen that there is some deviation for the larger source-detector separation (FIG. 7B) around the Soret band of hemoglobin absorption (420 nm).

Figure 8:
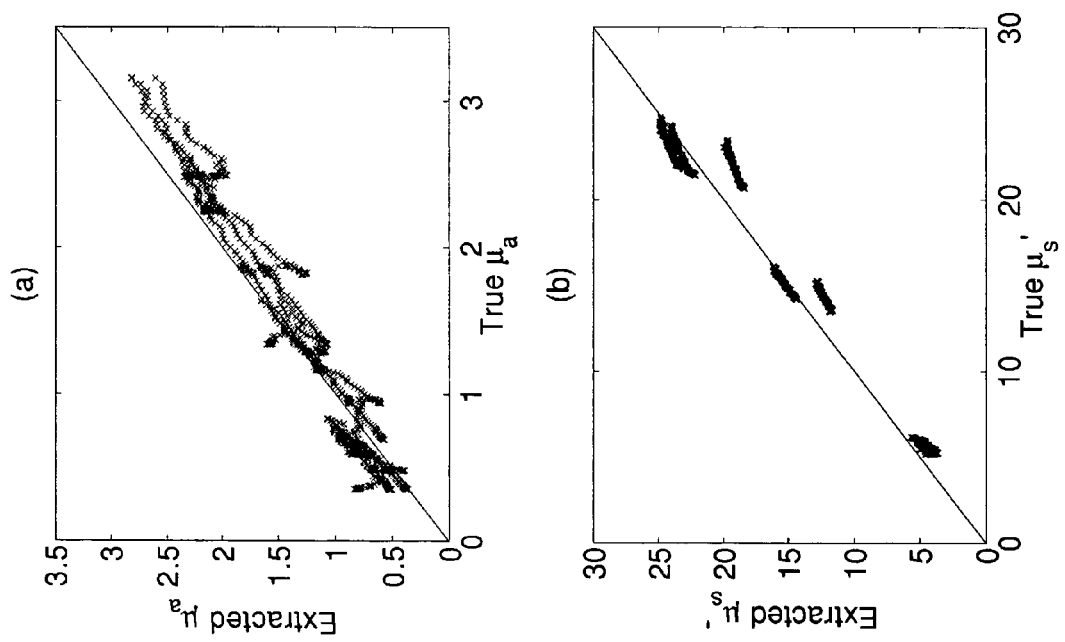
FIGS. 8A and 8B are scatter plots of the extracted vs. true absorption coefficient (FIG. 8A) and for the reduced scattering coefficient (FIG. 8B) for experimental studies over the wavelength range 450-616.

Finally, the region of discrepancy was excluded by limiting the wavelength range to be from 450-616 nm. FIG. 8 shows the extracted vs. true $\mu_a$ (FIG. 8A) and $\mu_s'$ (FIG. 8B), again using the phantom with scattering level 2 and absorption level 2 as the reference phantom. It can be seen that there is substantial agreement between the extracted and true optical properties over this limited wavelength range, resulting in a substantial improvement in the accuracy, albeit over a smaller range of absorption coefficients. The RMSE for the data shown in FIG. 8 is 0.2 cm$^{-1}$ and 1.4 cm$^{-1}$ for $\mu_a$ and $\mu_s'$, respectively. Repeating this for all possible reference phantoms, and averaging the RMSE yielded mean RMSEs of 0.4±0.1 cm$^{-1}$ and 2.2±0.6 cm$^{-1}$ for $\mu_a$ and $\mu_s'$, respectively. The phantoms had a range of 0.35-3.2 cm$^{-1}$ and 5.2-25 cm$^{-1}$ for $\mu_a$ and $\mu_s'$, respectively, over this narrower wavelength range.

Example 5

Derivation of Equation (3)

Equation (3) can be used to derive the probability that a photon launched into a circular illumination fiber of radius $r_i$, which travels a given net distance $r_t$, will be collected by a separate circular fiber of radius $r_c$ at a fixed center-to-center distance s from the illumination fiber. This probability can be derived for uniform fiber illumination and collection efficiencies. Both fibers are normal to the medium, which produces a circularly symmetric and translationally invariant system, assuming a homogeneous or homogeneous layered medium. Let the illumination fiber be centered at the origin, and the collection fiber be centered at (s, 0). First, the case in which photons are launched only at the center of the illumination fiber is considered. Because the system is circularly symmetric, the photon can exit the surface anywhere along the circle centered at the origin, with radius $r_t$, with equal probability. The probability that the photon will exit within the region contained by the collection fiber, and thus be collected, is given by $p=r_t\theta/2\pi r^2$, which corresponds to the arc length contained within the collection fiber, divided by the total circumference of the circle that defines all possible exit locations. This can be shown to be $$p = \frac{1}{\pi}\cos^{-1}\left(\frac{r_t^2 + s^2 + r_c^2}{2sr_t}\right), \quad (4)$$

$$s - r_c < r_t < s + r_c,$$

$$p = 0, \text{ otherwise.}$$

This can then be extended to a line source located at y=0, and $-r_i \leq x \leq r_i$, by noting that a displacement in x in the source effectively changes the source-detector separation s and then integrating. This is normalized to the length of the source line to produce the average probability for all source locations from which the photon could originate. For the following derivations it was assumed that the mean probability of collection is nonzero: i.e., $s-r_t-r_c<r_t<s+r_i+r_c$. In this case the probability of collection is given by:

$$p = \frac{1}{2r_i}\frac{1}{\pi}\int_{lb}^{ub}\cos^{-1}\left[\frac{r_t^2+(s-x)^2-r_c^2}{2(s-x)r_t}\right]dx, \quad (5)$$

where ub=min($r_i$,s-$r_t$+$r_c$) and lb=max (-$r_i$, s-$r_t$-r). These bounds correspond to the launch locations for which the probability of collection is nonzero.

Finally, this system can be extended to a fiber source by noting that the probability of collection is the same for any source location at a given distance from the center of the collection fiber. Thus each point in the integral given in Eq. (5) is weighted by the arc length of all source locations occurring within the source fiber, equidistant to the collection fiber center. The integral is then normalized to the area of the source fiber to produce the average probability of collection for all possible source locations. This gives $$p = \frac{1}{\pi r_i^2}\frac{1}{\pi}\int_{lb}^{ub}(s-x)\cos^{-1}\left[\frac{s^2+(s-x)^2-r_i^2}{2(s-x)s}\right]\times \\ \cos^{-1}\left[\frac{r_t^2+(s-x)^2-r_c^2}{2(s-x)r_t}\right]dx, \quad (6)$$

with the bounds of the integral being the same as those given hereinabove.

DISCUSSION OF THE EXAMPLES

The outcome of the fiber-optic probe design strategy described herein comprises a fairly simple illumination and collection geometry that is capable of extracting the optical properties of a medium from the diffuse reflectance spectra with RMSEs of 0.41 cm$^{-1}$ (tested range of 0-80 cm$^{-1}$) and 0.30 cm$^{-1}$ (tested range of 3-40 cm$^{-1}$), for $\mu_a$ and $\mu_s'$, respectively. Upon experimental validation of this algorithm using phantom studies, it was found that the algorithm did not perform as expected at high $\mu_a$, with RMSEs of 2.4 cm$^{-1}$ (tested range of 0.35-23) and 3.7 cm$^{-1}$ (tested range of 5.2-26), for $\mu_a$ and $\mu_s'$, respectively. It also was found that when the wavelength range was restricted to wavelengths greater than 450 nm, the experimental accuracy was similar to that of the simulation studies, with RMSEs of 0.4 cm$^{-1}$ (tested range of 0.35-3.2) and 2.2 cm$^{-1}$ (tested range of 5.2-25), for $\mu_a$ and $\mu_s'$, respectively.

It was noted that the case where the illumination fiber was also used for collection produced somewhat lower accuracy than the case where it was not. This could be due to the fact that the Henyey-Greenstein phase function was used to describe light transport for a very small volume in the case of the overlapping probe geometry. This phase function allows one to fix only the first moment of anisotropy, however, it has been shown that higher order moments of anisotropy must be accounted for when scaling Monte Carlo simulations at short source-detector separations (Thueler et al. (2003) 8 *J Biomed Opt* 495-503), as is the case when the source and collection fibers are overlapping. Incorporation of a more complex phase function could potentially improve this result. However, given that the separate collection fiber designs perform well, and the technical difficulties in eliminating specular reflection with a common source-collection fiber, the separate collection fiber design might be a preferred solution.

The success of this method is dependent on the ability to construct a fiber probe meeting the design specifications produced by the optimization algorithm. Errors in the positioning of the individual fibers introduced in the construction of this probe are thus a potential source of error. To minimize this, two design constraints were introduced. First the probe geometry was limited to a simple design consisting of a single illumination fiber and a variable number of collection fibers. This ensured that the resulting probe would be easily manufactured. Second, the fibers were placed in direct contact with the tissue, with no shield or casing to allow easy access for visualizing the fiber tips. This enables one to image the tip of the probe, and determine the exact positions of the individual fibers in the probe. In addition, it was found that for a reasonable range of positioning errors, the accuracy of this method in extracting optical properties was not adversely affected, provided the positioning errors were accounted for in this way.

In the optimal probe geometry, it was noted that one of the collection fibers (at 1.36 mm separation) was relatively insensitive to changes in the scattering properties of the medium. This fiber is similar in separation to that reported by Mourant et al. (1.7 mm; 36 *Appl Opt* 5655-5661, 1997), who found that at similar source-detector separations, the reflectance measured had a path length that was insensitive to changes in scattering. This fiber thus has the useful property of providing a direct reflection of the absorption properties of the medium. In the optimal probe geometry reported here, this was combined with a shorter source-detector separation (380 µm). At this shorter source-detector separation, the reflectance collected by the probe was insensitive to changes in $\mu_a$. This fiber thus provides a direct reflection of the albedo of the medium. Combining these two measurements enables a complete description of the optical properties of the medium.

Experimental validation of this approach yielded results that did not quite perform as well as the simulations had suggested. The primary source of this discrepancy was identified as the large deviation of the Monte Carlo simulations from the diffuse reflectance measured at the larger source detector separation, having a maximum error of 39 fold for the larger wavelength range (400-616 nm), and 87% for the smaller wavelength range (450-616 nm).

There are two likely explanations for this effect. First, the signal collected at high $\mu_a$ was extremely weak, particularly for the larger source detector separation, suggesting a limitation due to signal to noise issues. As a result, the signal collected may have been outside the linear dynamic range of the CCD detector. A wide range of integration times were used in an attempt to compensate for this, however there was still difficulty in obtaining sufficient signal at the Soret band of hemoglobin absorption without saturating adjacent portions of the spectra for the highest concentrations of hemoglobin.

A second potential source of error is in the construction of the fiber optic probe. At the common end of this probe, a metal spacer was used between the collection fibers at small and large separations. This has the effect of making the surface of the medium more reflective once photons extend beyond shorter source detector separation. Simonson et al. have reported that increasing the reflectivity of the probe between the source and collection fibers has the effect of reducing the mean probing depth of the collected photons (Simonson et al. (2006) 11 *J Biomed Opt* 014023). This would have the effect of shortening the mean path length and reducing the effect of absorption. In the Monte Carlo simulations, the entire surface of the medium above the phantom was modeled as an optical fiber in order to enable the use of scaling relationships. Thus, the effect reported by Simonson et al. could influence the deviation observed between the measured and Monte Carlo simulation for the larger source detector separation.

Certain experimental problems might need to be addressed before accurate retrieval of optical properties over the 400-450 nm wavelength range will be possible in tissue. However and as disclosed herein, the presently disclosed method showed reasonable accuracy for wavelengths longer than 450 nm, which has previously been demonstrated to be sufficient for the retrieval of hemoglobin concentrations (Finlay & Foster (2004) 31 *Med. Phys* 1949-59), and can also be used to characterize carotene absorption (Palmer et al. (2006) 45 *Appl Opt* 1072-1078). Thus, any possible inaccuracies in the range of 400-450 nm would not be expected to compromise the capability of this method for many biomedical applications where biological absorber concentrations need to be obtained.

A number of other studies have also investigated the extraction of optical properties from diffuse reflectance spectra (Thueler et al. (2003) 8 *J Biomed Opt* 495-503; Amelink et al. (2004) 29 *Opt Lett* 1087-1089; Palmer & Ramanujam (2006) 45 *Appl Opt* 1062-1071; Finlay & Foster (2004) 31 *Med Phys* 1949-1959; Zonios et al. (1999) 38 *Appl Opt* 6628-6637; Ghosh et al. (2001) 40 *Appl Opt* 176-184; Pfefer et al. (2003) 8 *J Biomed Opt* 206-215). These studies can be broken down into two general categories: (1) those using multiple fibers in the probe (six or more collection channels) to take advantage of the spatially resolved diffuse reflectance of a turbid medium to extract the optical properties (e.g., (Thueler et al. (2003) 8 *J Biomed Opt* 495-503; Ghosh et al. (2001) 40 *Appl Opt* 176-184; Pfefer et al. (2003) 8 *J Biomed Opt* 206-215), and (2) those studies that use relatively simple probe geometries (two or fewer independent collection channels), to extract the optical properties from the diffuse reflectance by making assumptions concerning the tissue constituents, including the absorbers and scatterers present in the tissue (e.g., Amelink et al. (2004) 29 *Opt Lett* 1087-1089; Palmer & Ramanujam (2006) 45 *Appl Opt* 1062-1071; Finlay & Foster (2004) 31 *Med Phys* 1949-1959; Zonios et al. (1999) 38 *Appl Opt* 6628-6637).

It can be desirable to use a diffuse reflectance model that minimizes the complexity of the probe geometry, in order to maintain cost-effectiveness, and minimize the overall dimensions of the fiber-optic probe such that it can be easily adaptable to endoscopic measurements (as in case (2)). However, as demonstrated in Palmer et al. (2006) 45 *Appl Opt* 1072-1078, the requirement for a priori information about the tissue constituents can negatively impact the effectiveness of such diffuse reflectance models. In particular, an inaccurate description of the absorption spectrum of beta-carotene was shown to have a negative impact on the quality of the fits to the breast tissue diffuse reflectance spectra obtained using an inverse Monte Carlo based model of diffuse reflectance (Palmer et al. (2006) 45 *Appl Opt* 1072-1078). The optimized approach employed in this study allows one to obtain the advantages of each approach by obtaining accurate optical property information using a simple probe geometry while requiring no a priori information about the tissue constituents.

This paper focused on optimizing the probe geometry for a specific application: i.e., reflectance-based extraction of optical properties for a semi-infinite medium. However, the methodology presented could be easily adapted to a number of other applications. By modifying the objective function appropriately, this approach could be employed to optimize a probe to meet any quantifiable goal, such as limiting the probing depth, or extracting the optical properties from the top layer of a layered medium. Furthermore, alternative methods of extracting optical properties could be used, such as the diffusion equation or Monte Carlo models instead of the neural network algorithm. These approaches would generally require that a nonlinear least squares fit be applied to fit the reflectance spectrum to the modeled spectrum given a particular set of optical properties (Palmer & Ramanujam (2006) 45 *Appl Opt* 1062-1071). This would have the advantage of using an established light transport model to relate the diffuse reflectance to the underlying optical properties.

However, these alternative methods are iterative in nature and thus would be much slower (likely several orders of magnitude) in both the optimization and extraction phases. In addition, while the EXAMPLES focus on the UV-VIS spectral range, these methods disclosed herein would also be applicable to the near infrared (NIR). In fact, the application to the UV-VIS is likely the more difficult task due to the wider range of optical properties present in biological samples. Finally, this approach could also be applied to fluorescence spectroscopy for the extraction of intrinsic fluorescence properties. This approach could be used to determine the optimal fiber probe design for essentially any spectroscopic application.

Although degree of matching between produced optical properties with known optical properties for given diffuse reflectance was used as the optimization metric in the experiments described above, the subject matter described herein is not limited to using this optimization criterion. Other optical properties that can be used for optimization of probe design include sensing depth of a probe geometry, sensing volume or spatial resolution of a probe geometry, measurement of physical properties of tissue, measurement of fluorescence properties of tissue, or measurement of any optical signal, such as but not limited to Raman scattering. In addition, the subject matter described herein is not limited to using a genetic algorithm to select the optimal probe geometry. Any selection algorithm, such as the gradient methods described above, may be used to select the optimal probe geometry.

The disclosure of each of the publications referenced herein is hereby incorporated by reference in its entirety.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for optimizing a probe geometry for spectroscopic measurement in a turbid medium, the method comprising:
   using a computer programmed to perform the following steps:
   (a) selecting a probe geometry comprising at least one emitting entity for emitting electromagnetic radiation into a turbid medium and at least one collecting entity for collecting the electromagnetic radiation that has interacted with the turbid medium;
   (b) performing a simulation of a light transport model with inputs of the probe geometry and a plurality of sets of optical property values associated with the turbid medium to generate output comprising optical parameter values that would be measured by the probe geometry for each set of input optical property values;
   (c) providing the measured optical parameter values as input to an inversion algorithm that produces optical properties corresponding to the measured optical parameter values generated by the simulation of the light transport model as output;

(d) comparing the optical properties produced by the inversion algorithm with the plurality of sets of optical properties known to correspond to the measured optical parameter values and determining a degree of matching between the produced and known optical properties;

(e) repeating steps (b)-(d) for a plurality of additional probe geometries, wherein each additional probe geometry differs from the probe geometry of step (a) in at least one property selected from the group consisting of a quantity of collecting entities, a diameter of at least one collecting entity, a linear distance between the emitting entity and the collecting entity, and combinations thereof, wherein repeating steps (b)-(d) comprises, at each iteration, applying an optimization algorithm to select a probe geometry such that the resulting degree of matching will converge to an optimum value; and (f) selecting from among the different probe geometries, an optimal geometry for the turbid medium based on the degree of matching determined for each geometry in step (d).

2. The method of claim 1, wherein the emitting entity is not a collecting entity.

3. The method of claim 1 wherein the emitting and collecting entities comprise optical fibers.

4. The method of claim 1, wherein the simulation employs a Monte Carlo model.

5. The method of claim 1, wherein the sets of optical properties include scattering coefficients ($\mu_s$), absorption coefficients ($\mu_a$), and anisotropy factors (g).

6. The method of claim 1, wherein the optical parameter values are selected from the group consisting of diffuse reflectance values, sensing depths of a probe geometry, sensing volume or spatial resolution of a probe geometry, measurements of a physical property of a tissue, measurements of a fluorescent property of a tissue, measurement of Raman scattering, and combinations thereof.

7. The method of claim 6, wherein the optical parameter values are diffuse reflectance values.

8. The method of claim 1, wherein each emitting and collecting entity of the probe has a diameter selected from the group consisting of 50, 100, 150, 200, 300, 400, and 500 μm.

9. The method of claim 1, wherein the turbid medium comprises a group of cells or a tissue in a subject or isolated from a subject.

10. The method of claim 9, wherein the group of cells or the tissue comprises a tumor or a tumor biopsy.

11. The method of claim 1, wherein the method simultaneously and/or consecutively optimizes the probe in terms of fiber diameter and distance from the emitting entity to each collecting entity.

12. The method of claim 1, wherein the inversion algorithm is executed by a neural network.

13. The method of claim 12 comprising training the neural network using a training set of optical parameter values and the corresponding known optical properties.

14. The method of claim 1, wherein the optimization algorithm comprises a genetic algorithm.

15. The method of claim 14, wherein the genetic algorithm comprises a component selected from the group consisting of a crossover operator, a mutation operator, and combinations thereof.

16. The method of claim 1, wherein the probe geometry consists of from 1 to 5 collecting entities, inclusive.

17. The method of claim 1, wherein determining a degree of matching between the produced and known optical properties comprises:

(a) determining a root mean square error (RMSE) for a parameter selected from the group consisting of absorption coefficient ($\mu_a$) and reduced scattering coefficient ($\mu_s'$; $=\mu_s \times (1-g)$, wherein $\mu_s$ is a scattering coefficient and g is an anisotropy factor) for each probe geometry; and (b) choosing a probe geometry for which the RMSE for each of $\mu_a$ and $\mu_s'$ is less than or equal to 0.5 cm$^{-1}$.

18. The method of claim 17, wherein choosing a probe geometry includes choosing a probe geometry for which the RMSE for each of $\mu_a$ and $\mu_s'$ is less than or equal to 0.45 cm$^{-1}$.

19. A system for selecting an optimal geometry for a probe for spectroscopic measurement in turbid media, the system comprising:

at least one processor programmed to implement:

(a) a light transport model configured to receive as inputs a probe geometry and a plurality of sets of optical properties of a turbid medium and configured to produce as output optical parameter values that would be measured by the probe geometry for each set of input optical properties;

(b) an objective function configured to implement an inversion algorithm that is configured to receive as input the measured optical parameter values, configured to produce corresponding optical properties, configured to compare the optical properties produced by the inversion algorithm with the plurality of sets of optical properties known to correspond to the measured optical parameter values, and configured to determine a degree of matching between the produced and known optical properties for the given probe geometry, wherein the light transport model and the inversion algorithm are adapted to test a plurality of different probe geometries and wherein the inversion algorithm is configured to determine a degree of matching between the produced and known optical properties for each geometry; and (c) a probe selector configured to select one of the geometries as an optimal geometry for the turbid medium based the degree of matching associated with the selected geometry.

20. The system of claim 19 wherein the probe selector is configured to iteratively select new probe geometries to be tested by the light transport model and the inversion algorithm and, at each iteration, to apply an optimization algorithm to select a probe geometry such that the resulting degree of matching will converge to an optimum value.

21. The system of claim 20 wherein the optimization algorithm comprises a genetic algorithm.

22. A computer program product comprising computer executable instructions embodied in a non-transitory computer readable medium for performing steps comprising:

(a) selecting a probe geometry comprising at least one emitting entity for emitting electromagnetic radiation into a turbid medium and at least one collecting entity for collecting the electromagnetic radiation that has interacted with the turbid medium;

(b) performing a simulation of a light transport model with inputs of the probe geometry and a plurality of sets of optical property values associated with the turbid medium to generate output comprising optical parameter values that would be measured by the probe geometry for each set of input optical property values;

(c) providing the measured optical parameter values as input to an inversion algorithm that produces optical properties corresponding to the measured optical parameter values generated by the simulation of the light transport model as output;

(d) comparing the optical properties produced by the inversion algorithm with the plurality of sets of optical properties known to correspond to the measured optical parameter values and determining a degree of matching between the produced and known optical properties;

(e) repeating steps (b)-(d) for a plurality of additional probe geometries, wherein each additional probe geometry differs from the probe geometry of step (a) in at least one property selected from the group consisting of a quantity of collecting entities, a diameter of at least one emitting or collecting entity, a linear distance between the emitting and collecting entities, and combinations thereof, wherein repeating steps (b)-(d) comprises, at each iteration, applying an optimization algorithm to select a probe geometry such that the resulting degree of matching will converge to an optimum value; and (f) selecting, from among the different probe geometries, an optimal geometry for the turbid medium based on the degree of matching determined for each geometry in step (d).

* * * * *